(12) United States Patent
Ma et al.

(10) Patent No.: US 11,236,137 B2
(45) Date of Patent: Feb. 1, 2022

(54) **RECOMBINANT *DERMATOPHAGOIDES FARINAE* TYPE 2 ALLERGEN PROTEIN AND ITS PREPARATION METHOD AND APPLICATION**

(71) Applicant: ZonHon Biopharma Institute, Inc., Jiangsu (CN)

(72) Inventors: Bruce Yong Ma, Jiangsu (CN); Yu Fan, Jiangsu (CN); Jun Wang, Jiangsu (CN); Anliang Wang, Jiangsu (CN)

(73) Assignee: ZonHon Biopharma Institute, Inc., Jiangsu (CN)

( * ) Notice: Subject to any disclaimer, the term of this patent is extended or adjusted under 35 U.S.C. 154(b) by 219 days.

(21) Appl. No.: 16/456,218

(22) Filed: Jun. 28, 2019

(65) Prior Publication Data

US 2019/0389918 A1 Dec. 26, 2019

Related U.S. Application Data

(63) Continuation of application No. PCT/CN2017/119200, filed on Dec. 28, 2017.

(30) Foreign Application Priority Data

Dec. 31, 2016 (CN) .......................... 201611267247.5

(51) Int. Cl.
*C07K 14/435* (2006.01)
*A61K 39/35* (2006.01)
*C12N 15/81* (2006.01)

(52) U.S. Cl.
CPC ........ *C07K 14/43531* (2013.01); *A61K 39/35* (2013.01); *C12N 15/815* (2013.01); *C12N 2800/22* (2013.01)

(58) Field of Classification Search
None
See application file for complete search history.

(56) References Cited

U.S. PATENT DOCUMENTS

| 2008/0274059 A1 | 11/2008 | Moingeon et al. |
| 2010/0086569 A1 | 4/2010 | Ross |
| 2016/0251403 A1 | 9/2016 | Lundegaard et al. |

FOREIGN PATENT DOCUMENTS

| CN | 1780852 A | | 5/2006 | |
| CN | 101595126 A | | 12/2009 | |
| CN | 102676568 A | | 9/2012 | |
| CN | 105848677 A | | 8/2016 | |
| WO | WO 1999/34826 | * | 7/1999 | ............. A61K 39/35 |
| WO | 2001/29078 A2 | | 4/2001 | |
| WO | WO 2003/047618 | * | 6/2003 | ............. A61K 39/35 |

OTHER PUBLICATIONS

Hu et al., Construction of prokaryotic expression system for the dust mite allergen Der f 2 in full-length and analysis of its structure and function. Chinese Immunology Journal 27(6): 533-539 (2011).
UniProtKB Accession No. Q00855. RecName: Full=Mite group 2 allrgen Der f 2; AltName: Full=Allergen Der f II AltName: Allergen=Der f 2; Flags: Precursor. 4 pages, Sep. 18, 2019.
Yuuki et al., Cloning and expression of cDNA coding for the major house dust mite allergen Der f II in *Escherichia coli*. Agric Biol Chem. May 1991;55(5):1233-8.
International Search Report and Written Opinion for Application No. PCT/CN2017/119200, dated Mar. 30, 2018, 19 pages.
GenBank Accession No. EF139432, Dermatophagoides farinae clone 2 Der f 2 allergen mRNA, complete cds. 2 pages, Jun. 4, 2007.
Lu, Research Progress of Pichia pastoris expression system and its secreted protein expression. Journal of Chinese and Experimental Medicine. Mar. 2014; 3(1):43-47.
Zhao et al., Synonymous Codon Usage in Pichia pastoris. Chinese Journal of Biotechnology. May 2000;16(3):308-311.

* cited by examiner

*Primary Examiner* — Nora M Rooney
(74) *Attorney, Agent, or Firm* — McCarter & English, LLP; Yu Lu

(57) ABSTRACT

Provided are an optimized Der f2 gene, a recombinant Der f2 protein encoded thereby, a vector comprising said gene, and a *Pichia pastoris* strain. Also provided are an expression method, a purification method, and an application of the recombinant Der f2 protein.

8 Claims, 17 Drawing Sheets

Specification includes a Sequence Listing.

| | | |
|---|---|---|
| Sequence before optimization | 1 | ATGATTTCCAAAATCTTGTGCCTTTCATTGTTGGTAGCAGCCGTTGTTGCCGATCAAGTC |
| | | ||||| || || |||||||| | || |||||||| || || |||||||| || || || |
| Sequence after optimization | 1 | ATGATCTCTAAGATCTTGTGTTTGTCTTTGTTGGTTCCTGCTGTTGTTGCTGACCAGGTT |
| | 61 | GATGTTAAAGATTGTGCCAACAATGAAATCAAAAAAGTAATGGTCGATGGTTGCCATGGT |
| | | || |||||| || ||||| ||||| || ||||| ||||| ||||| || ||||| || ||| |
| | 61 | GACGTTAAGGACTGTGCTAACAACGAGATCAAGAAAGTTATGGTTGACGGTTGTCACGGT |
| | 121 | TCTGATCCATGCATCATCCATCGTGGTAAACCATTCACTTTGGAAGCCTTATTCGATGCC |
| | | || || |||||| || || || | ||||| |||||||||||||| || || ||||| || |
| | 121 | TCCGACCCATGTATTATTCACAGAGGTAAGCCATTCACTTTGGAGGCTTTGTTCGACGCT |
| | 181 | AACCAAAACACTAAAACCGCTAAAATTGAAATCAAAGCCAGCCTCGATGGTCTTGAAATT |
| | | ||||| |||||||| || |||||| || || || || || | | || ||| | || ||| |
| | 181 | AACCAGAACACTAAGACTGCTAAGATCGAGATTAAGGCTTCCTTGGACGGTTTGGAGATT |
| | 241 | GATGTTCCCGGTATCGATACCAATGCTTGCCATTTTATGAAATGTCCATTGGTTAAAGGT |
| | | || |||||| |||||||| || || ||||| || |||||||| ||||||||||||| ||| |
| | 241 | GACGTTCCAGGTATCGACACTAACCCTTGTCACTTTATGAAGTGTCCATTGGTTAAGGGT |
| | 301 | CAACAATATGATATCAAATATACATGGAATGTGCCGAAAATTGCACCAAAATCTGAAAAC |
| | | || || || || |||||| || || |||||||| || || || || ||||| || || ||| |
| | 301 | CAGCAGTACGACATCAAGTACACTTGGAATGTTCCAAAGATCGCTCCAAAGTCCGAGAAC |
| | 361 | GTTGTCGTTACAGTCAAACTTATCGGTGATAATGGTGTTTTGGCTTGCGCTATTGCTACC |
| | | ||||| ||||| || || | |||||||| || |||||||||||||| |||||||||| |
| | 361 | GTTGTTGTTACTGTTAAGTTGATCGGTGACAACGGTGTTTTGGCTTGTGCTATTGCTACT |
| | 421 | CATGGTAAAATCCGTGATTAA |
| | | || ||||| ||| | |||||| |
| | 421 | CACGGTAAGATCAGAGATTAA |

FIG. 1

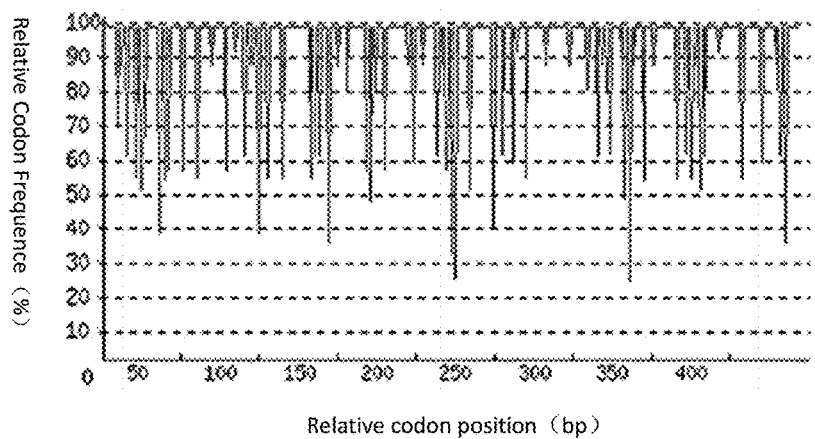

FIG. 2A

Relative codon position (bp)

Relative codon position (bp)

Standard amino acid profiles
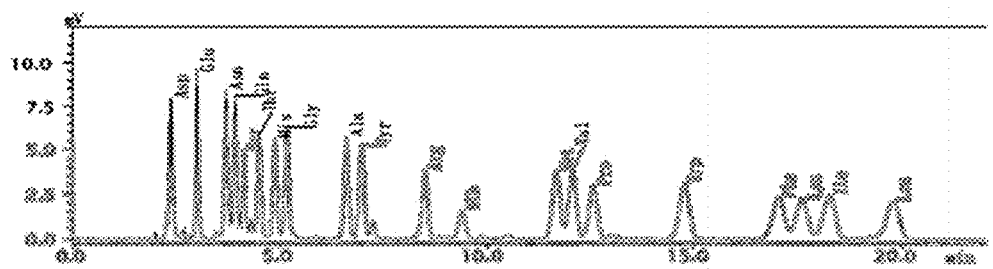
Mass Spectrogram of the Five Amino Acids at the N-terminal of Protein
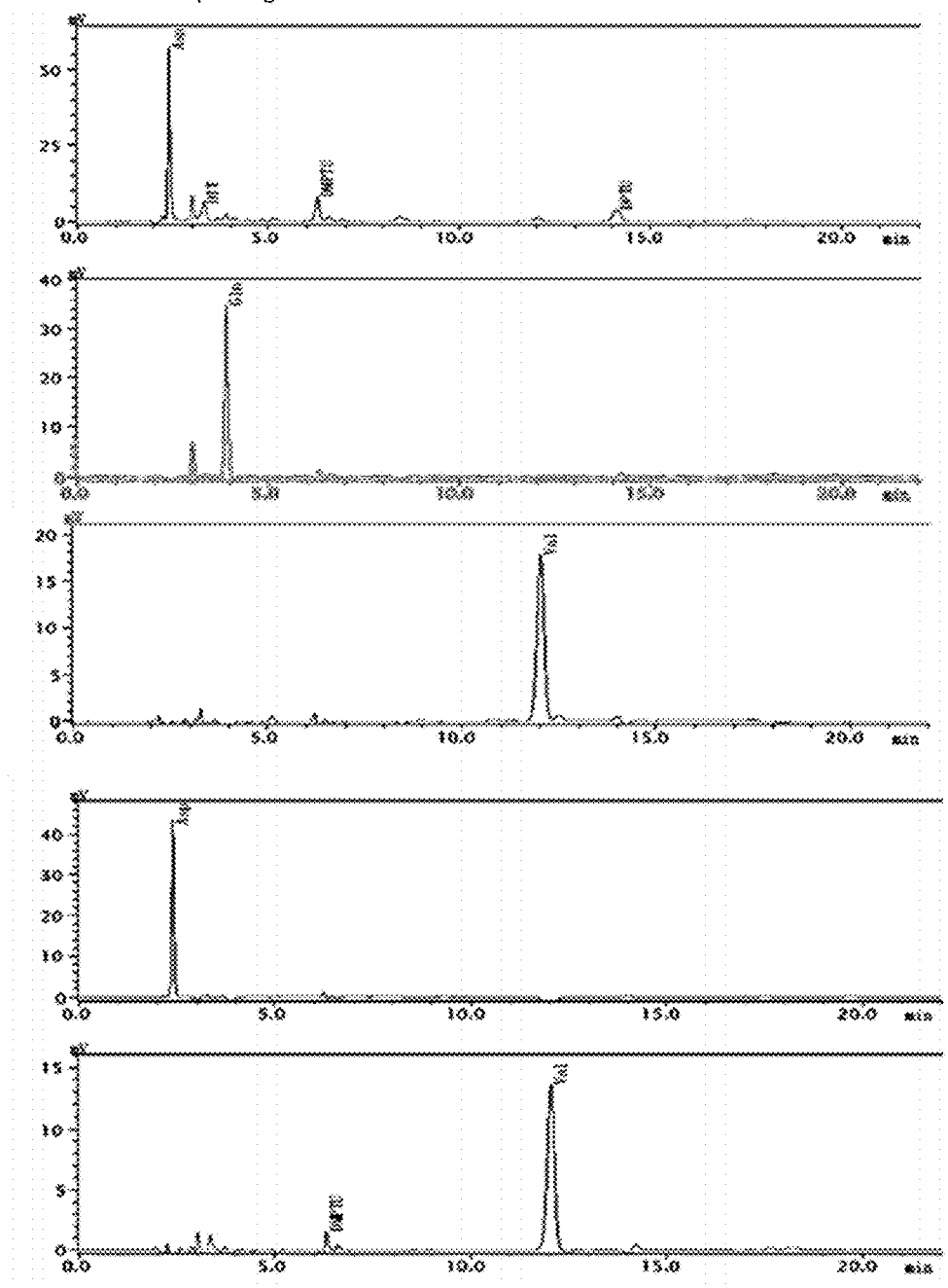
FIG. 11

RECOMBINANT *DERMATOPHAGOIDES FARINAE* TYPE 2 ALLERGEN PROTEIN AND ITS PREPARATION METHOD AND APPLICATION

REFERENCE TO RELATED APPLICATIONS

This application is a continuation application of International Patent Application No. PCT/CN2017/119200, filed on Dec. 28, 2017, and published as WO 2018/121640 A1, which claims priority to Chinese Patent Application No. CN201611267247.5, filed on Dec. 31, 2016. The entire contents of the above referenced applications, including the original specifications and drawings in Chinese, and any sequence listing, are hereby incorporated herein by reference.

SEQUENCE LISTING

The instant application contains a Sequence Listing which has been filed electronically in ASCII format and is hereby incorporated by reference in its entirety. Said ASCII copy, created on Sep. 19, 2021, is named Seq_Listing_131064-00401 and is 4,870 bytes in size.

TECHNICAL FIELD

The invention belongs to the field of bioengineering genes, and relates to a recombinant *Dermatophagoides farinae* type 2 allergen, and its coding gene and expression and purification method.

BACKGROUND OF THE INVENTION

There are many kinds of dust mites, which are widely present in human living and working environments. The excreta, metabolites and mite bodies of dust mites have strong allergenicity. According to statistics, about 10% of the world's population is allergic to dust mites, and about 80% of extrinsic asthma is caused by dust mites.

At present, a crude extract of dust mite allergens is mainly used clinically to treat allergic diseases caused by dust mites. For example, *Dermatophagoides* drops, named "Changdi", of Zhejiang Wolwopharma Co., which was marketed in 2006, is an extract of metabolic culture of *Dermatophagoides farinae*. Allergens of dust mites mainly exist in excreta and mite bodies; therefore, the extraction method takes a long time with a cumbersome process and a high cost. In addition, the composition of a natural allergen extract is very complicated, it is very difficult to make its components constant, and the natural allergen extract is easy to be contaminated by exogenous toxic substances and pathogenic microorganisms. Long-term use of a crude extract of dust mite allergens can lead to local reactions such as flush, swelling, induration and necrosis; and systemic reactions such as shock, edema, bronchospasm, urticaria, angioedema and systemic erythema. In addition, in the case that the crude extract is used for diagnosis, it is impossible to specifically determine the extent of the patient's response to each component of the allergens, which may lead to misdiagnosis.

The quality of the allergen is essential for the diagnosis and treatment of allergic diseases, and the allergen used for immunodiagnosis and immunotherapy should be a pure product rather than a crude extract. Recombinant allergens have the following advantages over crude extracts: (1) the recombinant allergens have a higher purity and contain no non-allergenic components, enzymes, enzyme inhibitors and toxic proteins as compared with the crude extracts; (2) the recombinant protein has a single composition, has good specificity, while the components in the crude extract are complex, the patient may only have reactions with some of the components of the crude extract, and the specificity is poor; (3) as compared with the natural extract, the recombinant allergen reduces IgE-bound antigenic epitopes and thus reduces IgE-mediated allergic reactions effectively, at the same time the domains of allergen necessary for T cell recognition are retained to result in better immunogenicity, thereby reducing the risk of immunotherapy and improving the desensitization therapy effect.

Allergens of dust mites are complex in composition, with more than 30 types, of which type 1 and type 2 allergens are the most important allergen components. In the serum of dust mite allergic patients, 70-80% of the patients had IgE binding to type 2 allergens, and showed strong positive reaction. The precursor of Der f2 was composed of 146 amino acids, and 129 amino acids remained after signal peptide removal. The molecular weight of Der f2 was 14 KD and there was no glycosylation site. At present, the representative of Der f2 recombinant expression is Hu Youying's research on prokaryotic expression system in 2011, and Cui Yubao's application in 2012 for "a method of producing recombinant *Dermatophagoides farinae* allergen Derf1 and Derf2 fusion protein" (China Patent No. CN102676568A). However, the prokaryotic expression system has no function of post-translational modification. The structure of Der f2 protein obtained is incorrect, and its reactivity with serum is weak, and it is difficult to isolate and purify it later.

SUMMARY OF THE INVENTION

In order to overcome the above-mentioned shortcomings, the inventors optimize the Der f2 gene in the *Pichia pastoris* expression system, and add an acting element to increase the expression of Der f2 in molecular level, and the inventors surprisingly find that Der f2 after gene optimization is expressed at a higher level as compared with the prior art, and has a similar biological activity as the natural protein.

One object of the present invention is to provide a DNA sequence encoding Der f2 protein, having a base sequence as shown in SEQ ID NO: 1. This sequence has been codon-optimized for the *Pichia pastoris* expression system, which is more conducive to expressing Der f2 in *Pichia pastoris*.

Another object of the present invention is to provide Der f2 protein having an amino acid sequence as shown in SEQ ID NO: 3.

Another object of the present invention is to provide a vector comprising the above-mentioned optimized gene encoding Der f2, preferably, the vector is pAO815, pPIC9, pPIC9K, pPIC3.5, pPIC3.5K, pPICZA, B, C or pGAPZA, B, C, more preferably pPIC3.5K, pPICZA or pGAPZA.

Another object of the present invention is to provide a *Pichia pastoris* strain comprising the above-mentioned vector, preferably, the *Pichia pastoris* strain is SMD1168, GS115, KM71, X33 or KM71H, more preferably strain KM71 or X33.

Preferably, there is 242 bp interval between the DNA sequence encoding the Der f2 protein and the ATG of AOX1 of *Pichia pastoris*; the DNA sequence encoding the Der f2 protein is preceded by Kozak sequence GCCACCATGG (SEQ ID No: 10).

Another object of the present invention is to provide a method for expressing the Der f2 protein, comprising the steps of:

A constructing a vector comprising the above-mentioned gene encoding Der f2;

B linearizing the vector of step A, transferring it into a *Pichia pastoris* strain, and culturing under a suitable condition;

C recovering and purifying the protein.

The above-mentioned vector is preferably pPIC3.5K, pPICZA or pGAPZA.

The above-mentioned *Pichia pastoris* strain is preferably a KM71 or X33 strain.

More preferably, the above-mentioned vector is pPICZA, and the above-mentioned *Pichia pastoris* strain is strain X33.

Another object of the present invention is to provide a method for purifying a recombinant Der f2 protein, comprising the steps of:

A centrifuging the Der f2 fermentation broth at a low temperature and a high speed to collect a supernatant, ultra-filtrating the supernatant against a 50 mM sodium acetate buffer at pH 4.0, and filtering through a 0.45 μm filter membrane;

B the first step, cation chromatography, comprising equilibrating a chromatographic column with an equilibration buffer, passing the Der f2 fermentation broth pretreated in step A through a separation packing using a purification system, and then eluting with a gradient of an elution buffer to collect an elution peak, wherein the equilibration buffer is 50 mM sodium acetate at pH 4.0, and the elution buffer is 50 mM sodium acetate and 1.0 M sodium chloride at pH 4.0;

C the second step, comprising ultra-filtrating the Der f2 protein peak collected in step B with a 20 mM phosphate solution at pH 6.0, equilibrating a chromatographic column with an equilibration buffer, loading the ultra-filtrated Der f2 protein solution on an anion chromatography packing, and collecting a flow-through peak, wherein the equilibration buffer is 20 mM phosphate at pH 6.0;

D the third step, comprising adding ammonium sulfate to the flow-through peak in step C to the final concentration of 1.5 M, pH 6.0, equilibrating a chromatographic column with an equilibration buffer, loading a Der f2 sample on a hydrophobic chromatography packing, eluting with a gradient of an elution buffer, wherein equilibration buffer is 1.5 M ammonium sulfate and 20 mM phosphate at pH 6.0, and the elution buffer is 20 mM phosphate at pH 6.0.

Another object of the present invention is to provide the use of the recombinant Der f2 protein in the preparation of a medicament for treating a dust mite allergic disease. The allergic disease is allergic rhinitis, allergic asthma, and the like.

The recombinant Der f2 protein of the present invention has a high expression level and has similar biological activity as the natural protein.

BRIEF DESCRIPTION OF THE DRAWINGS

FIG. 1 is a comparison plot of sequences of the recombinant Der f2 gene before and after optimization.

The sequence before optimization corresponds to the nucleotide sequence of the natural Der f2 gene; the sequence after optimization corresponds to the nucleotide sequence of the recombinant Der f2 gene of the present invention, that is, the codon-optimized sequence.

Figure 2B:
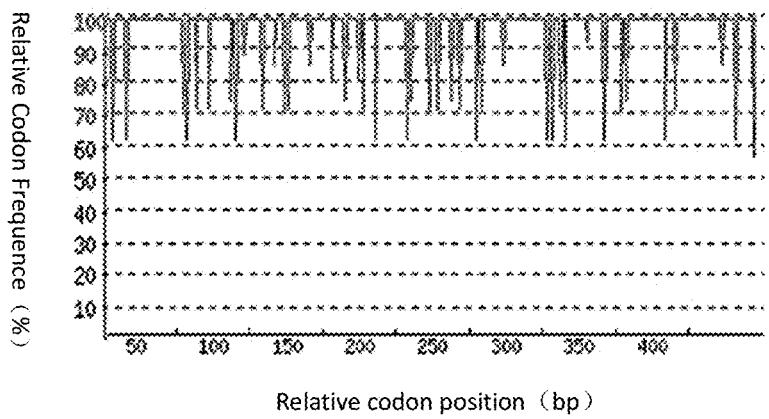

FIGS. 2A and 2B show the CAI indices of the Der f2 gene in the *Pichia pastoris* expression system before and after optimization.

FIG. 2A shows that the CAI index of the nucleotide sequence of the natural Der f2 gene in the *Pichia pastoris* expression system was calculated by a program to be 0.80. FIG. 2B shows that the CAI index of the optimized Der f2 codon of the present invention in the *Pichia pastoris* expression system is calculated by a program to be 0.90.

Figure 3A:
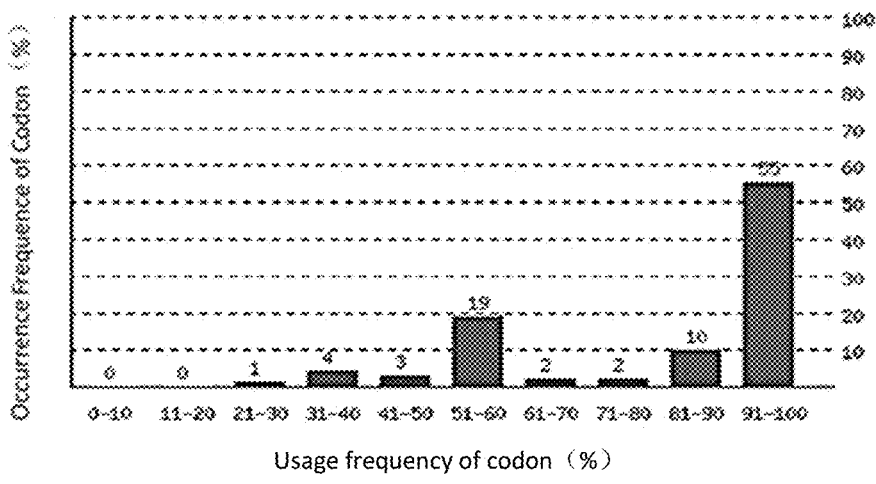
Figure 3B:
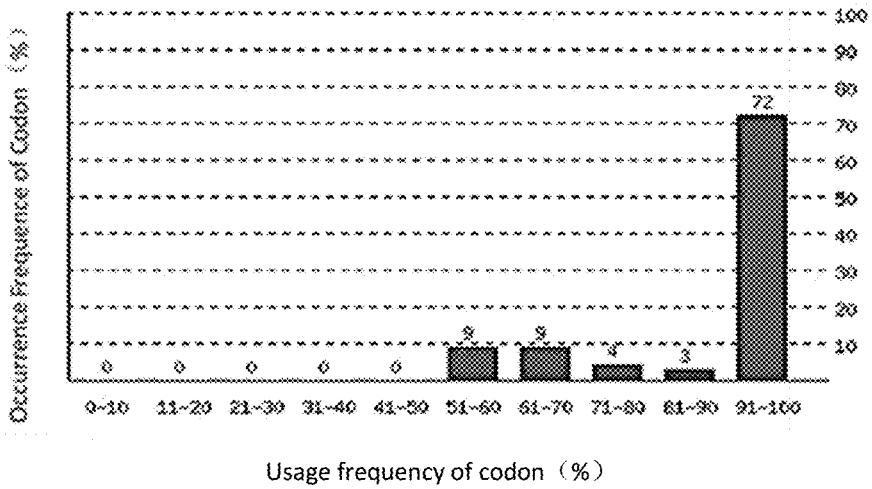

FIGS. 3A and 3B are optimal codon frequency distribution region plots of the Der f2 gene in the *Pichia pastoris* expression host before and after codon optimization.

FIG. 3A is an optimal codon frequency distribution region plot of the nucleotide sequence of natural Der f2 gene in the *Pichia pastoris* system, and it can be seen from the Figure that the occurrence percentage of low-utilization codon in the nucleotide sequence of natural Der f2 gene is 5%. FIG. 3B shows an optimal codon frequency distribution region plot of the optimized Der f2 codon of the present invention in the *Pichia pastoris* system, and the occurrence rate of low-utilization codon in the sequence of optimized Der f2 codon of the present invention is 0.

Figure 4A:
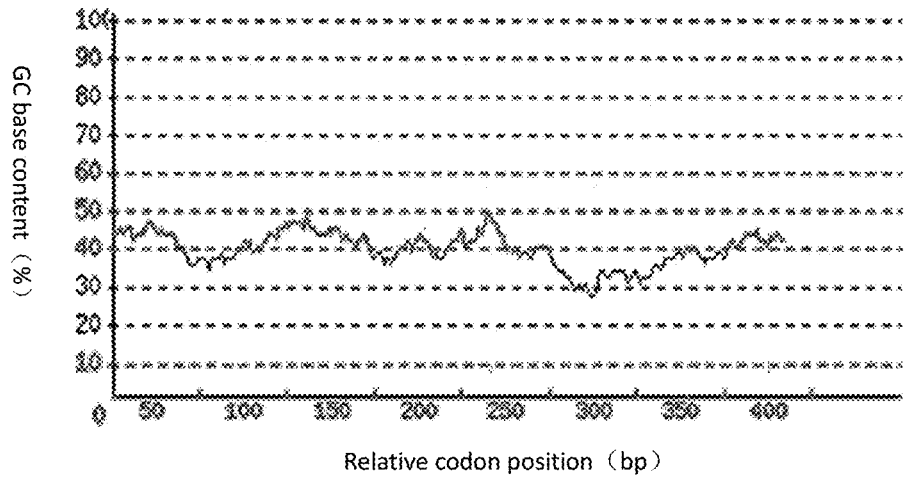
Figure 4B:
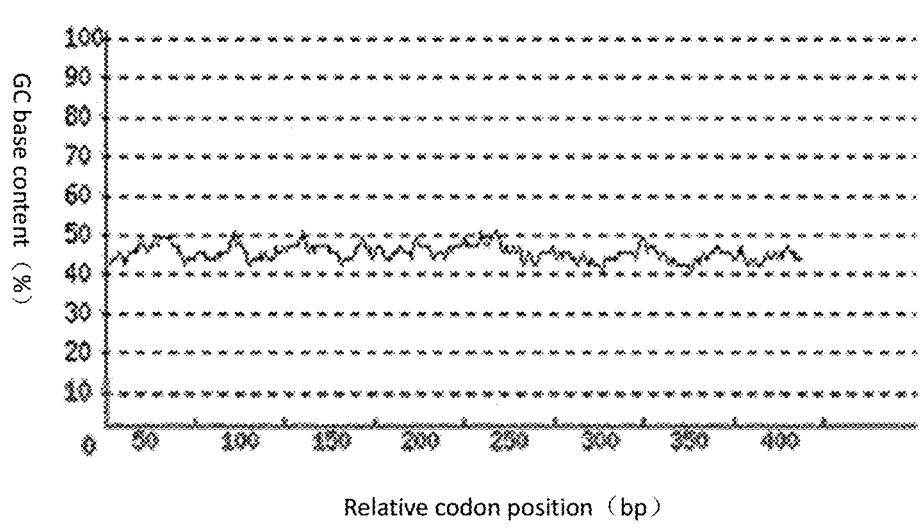

FIGS. 4A and 4B are average GC base content distribution region plots of the Der f2 gene in the *Pichia pastoris* expression system before and after codon optimization.

FIG. 4A shows that the average GC base content of the nucleotide sequence of the natural Der f2 gene in the *Pichia pastoris* expression system is 39.37%. FIG. 4B shows that the average GC base content of optimized Der f2 codon of the present invention in the *Pichia pastoris* expression system is 44.93%.

Figure 5:
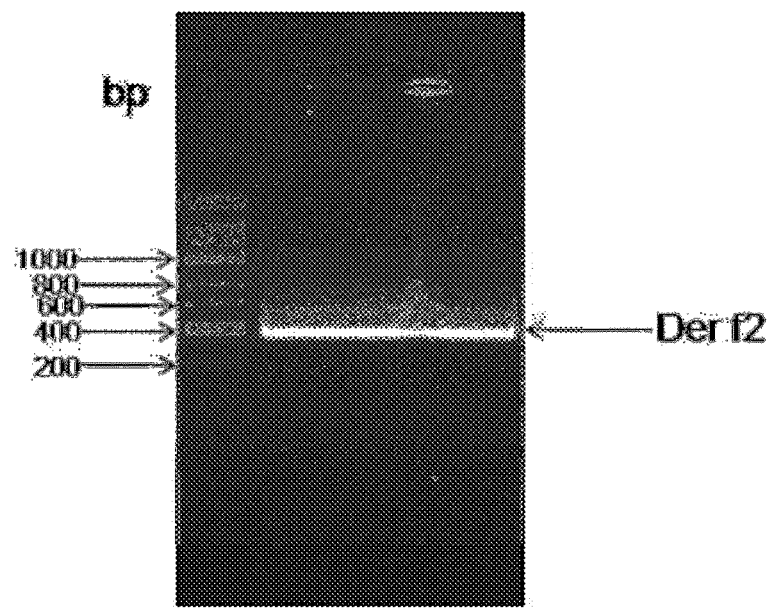

FIG. 5 is an agarose gel electrophoretogram of a PCR product of the codon-optimized Der f2 gene.

Lane 1 represents 500 bp DNA ladder; lane 2 represents a PCR product of the recombinant Der f2 gene containing EcoRI and XhoI restriction sites at both ends.

Figure 6:
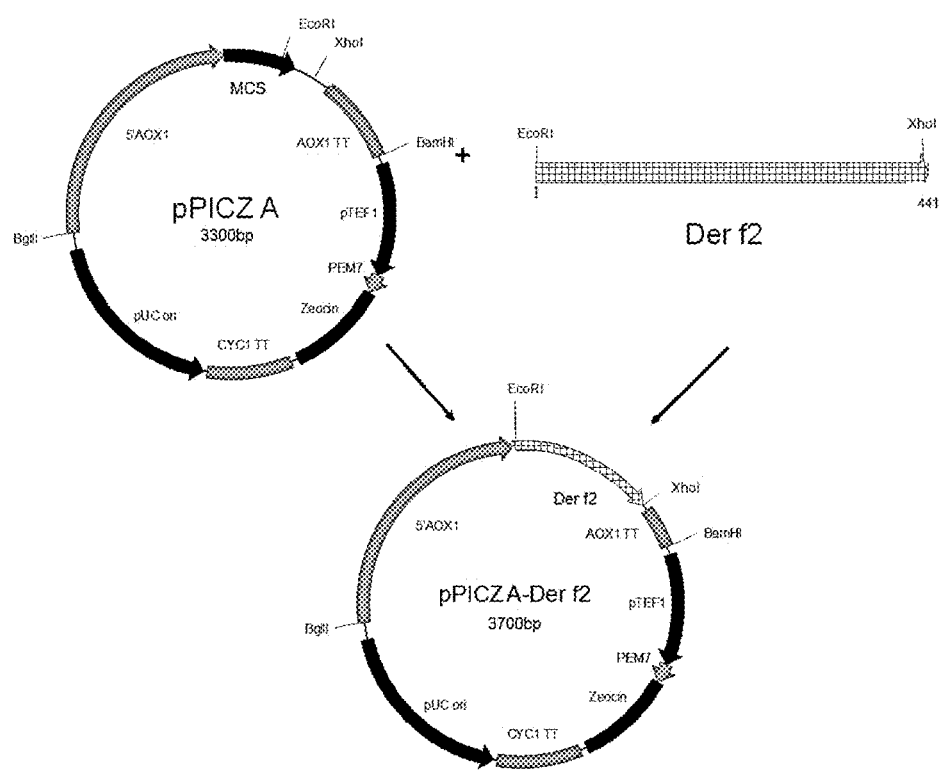

FIG. 6 is a diagram showing a construction process of the expression plasmid pPICZ-Der f2 for codon-optimized Der f2.

Figure 7A:
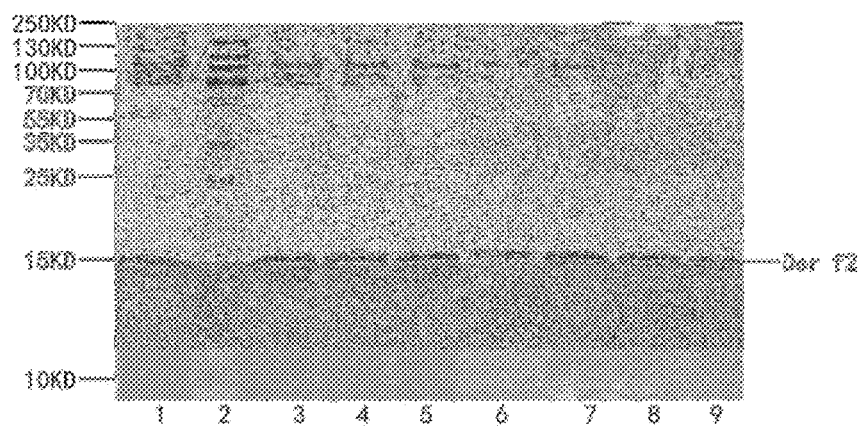
Figure 7B:
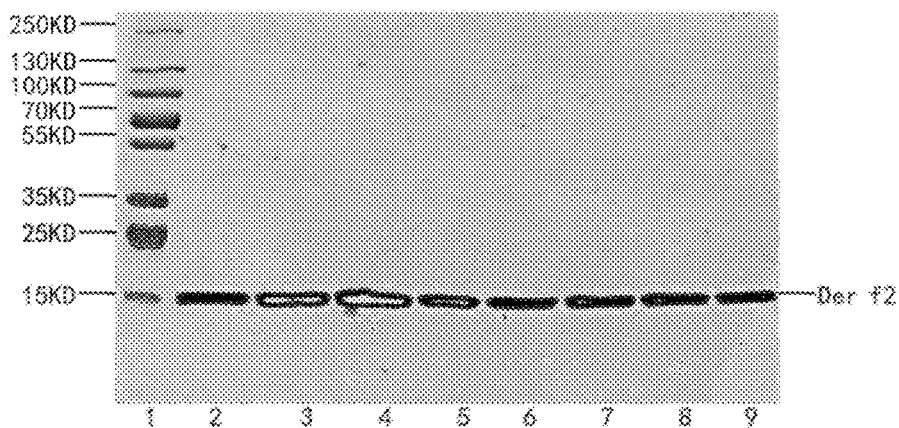

FIGS. 7A-7B are diagrams showing the identification of expression of the codon-optimized Der f2 gene in the host engineering bacteria.

FIG. 7A is a SDS-PAGE gel electrophoretogram of a supernatant of a solution of the host engineering strain containing the codon-optimized Der f2 gene, after methanol-induced expression for one week. Lane 2 represents pre-stained protein loading markers in the range of 10-250 KD; and other lanes represent supernatants of cultured solutions of Der f2 gene-positive monoclonal host engineering strains screened by Zeocin.

FIG. 7B is a western blot plot of a supernatant of a solution of the host engineering strain containing the codon-optimized Der f2 gene, after methanol-induced expression for one week. Lane 1 represents pre-stained protein loading markers in the range of 10-250 KD; and lanes 2-9 represent supernatants of cultured solutions of Der f2 gene-positive monoclonal host engineering strains screened by Zeocin.

Figure 8A:
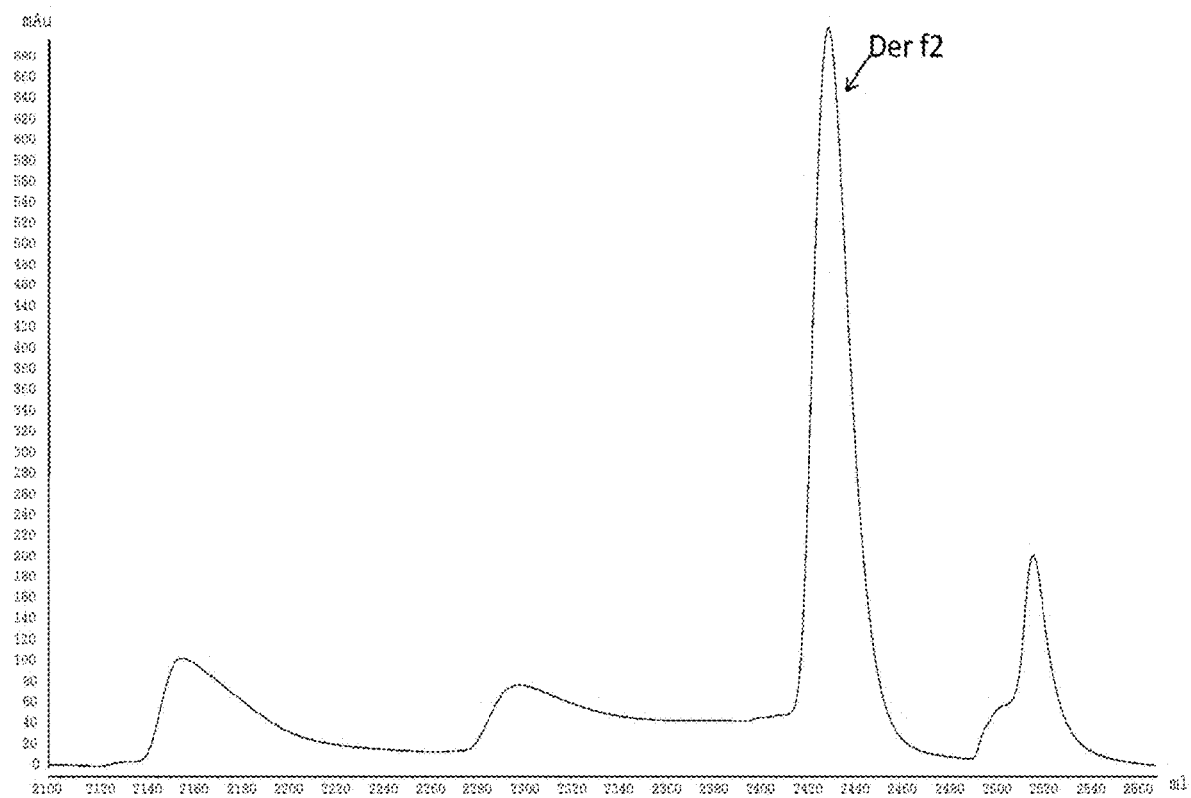
Figure 8B:
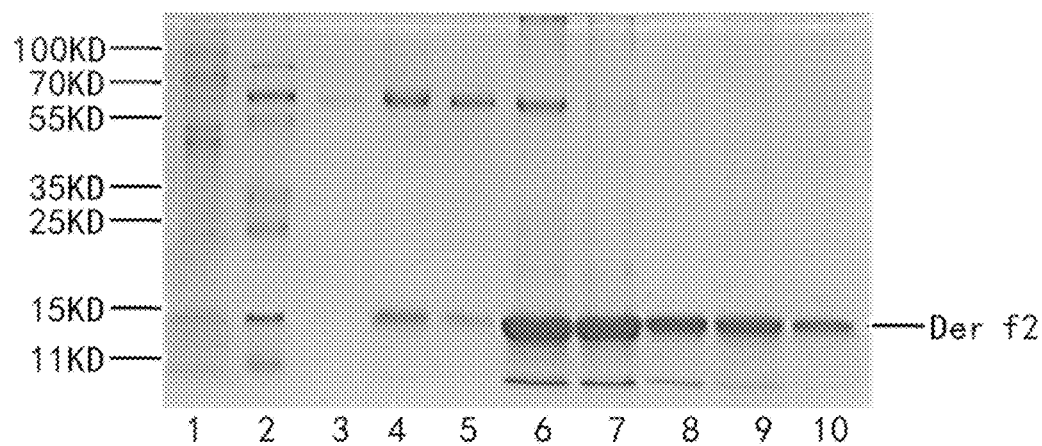

FIG. 8A shows a chromatogram of the supernatant of Der f2 fermentation broth by cation chromatography of the first step, and FIG. 8B is a gel electrophoretogram.

FIG. 8A is a chromatogram of the supernatant of Der f2 fermentation broth by cation chromatography of the first step. FIG. 8B is the identification result of cation chromatography purification of the supernatant of Der f2 fermentation broth, wherein lane 1 represents 11-100 KD non-pre-stained protein markers, lane 2 represents the supernatant of the Der f2 fermentation broth before purification, lane 3 represents the flow-through liquid, and lanes 4-10 represent the elution of each tube.

Figure 9A:
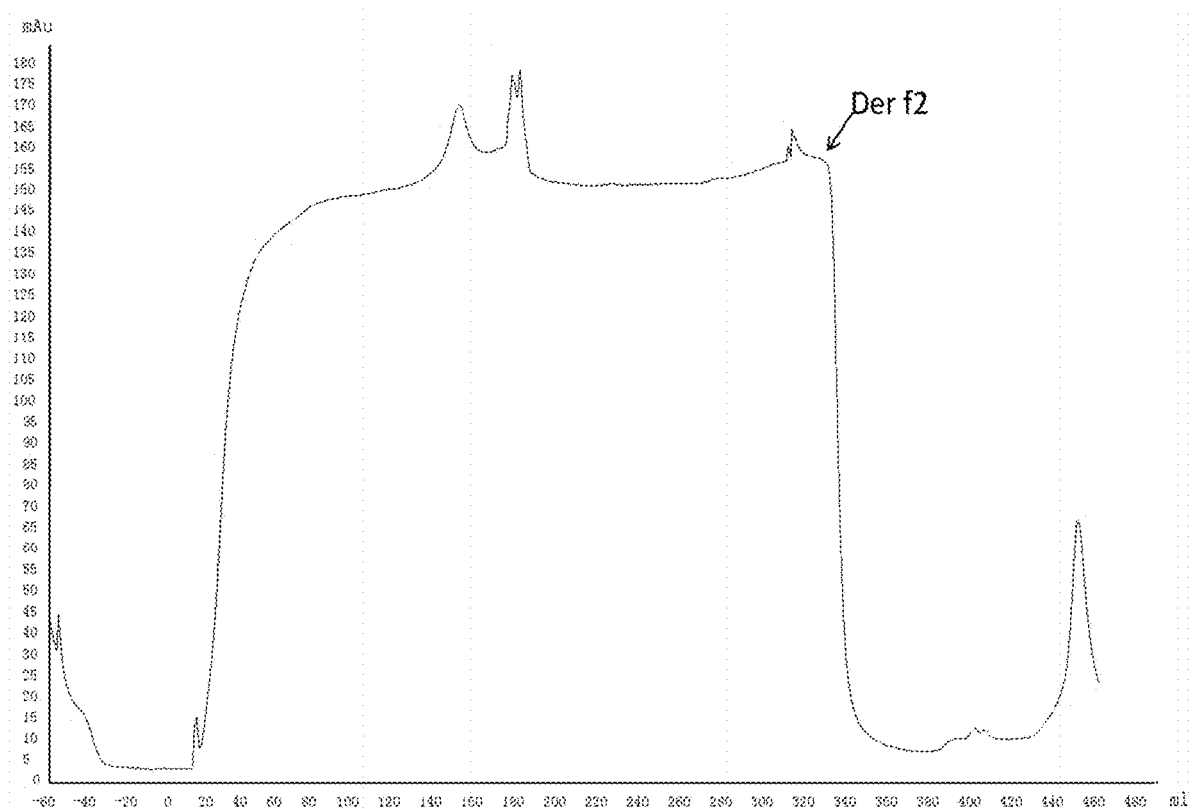
Figure 9B:
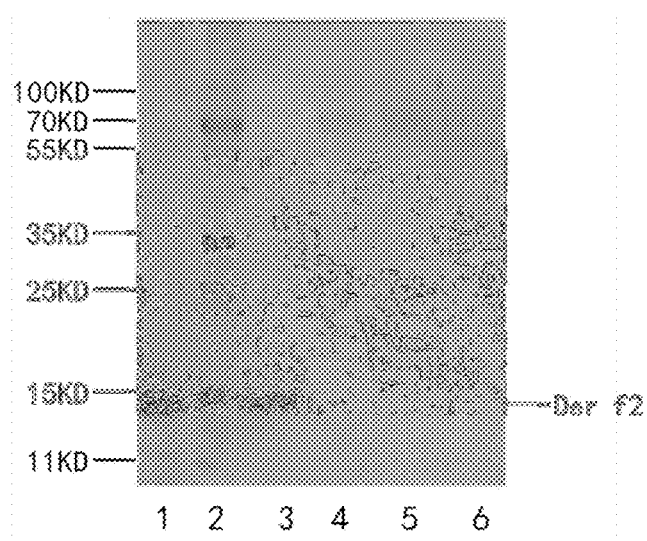

FIG. 9A is a chromatogram of Der f2 protein by anion chromatography of the second step, and FIG. 9B is a gel electrophoretogram.

FIG. 9A is a chromatogram of Der f2 protein by anion chromatography. FIG. 9B is the identification result of anion chromatography purification of Der f2 supernatant, wherein lane 2 represents 11-100 KD non-pre-stained protein markers, lane 1 represents the supernatant before purification of Der f2 protein, lane 2 represents the flow-through liquid of Der f2 protein, and lane 3-6 represent the elution of each tube.

Figure 10A:
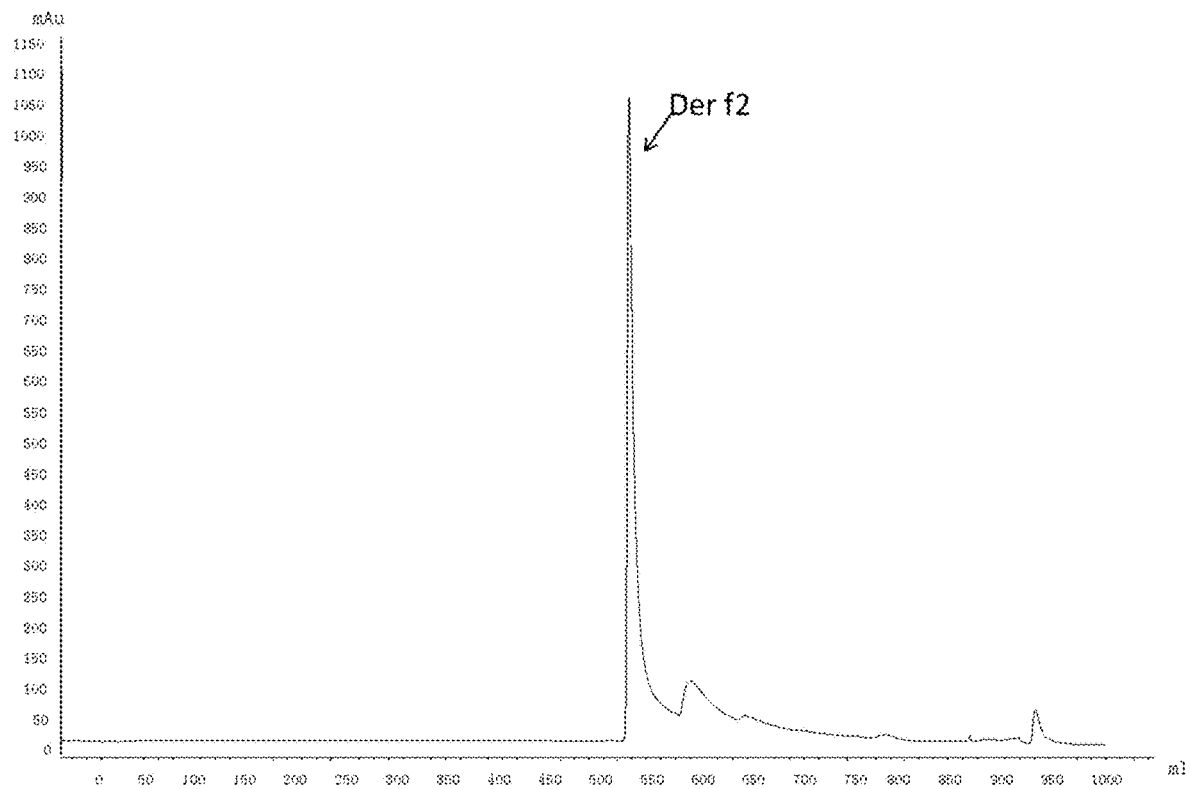
Figure 10B:
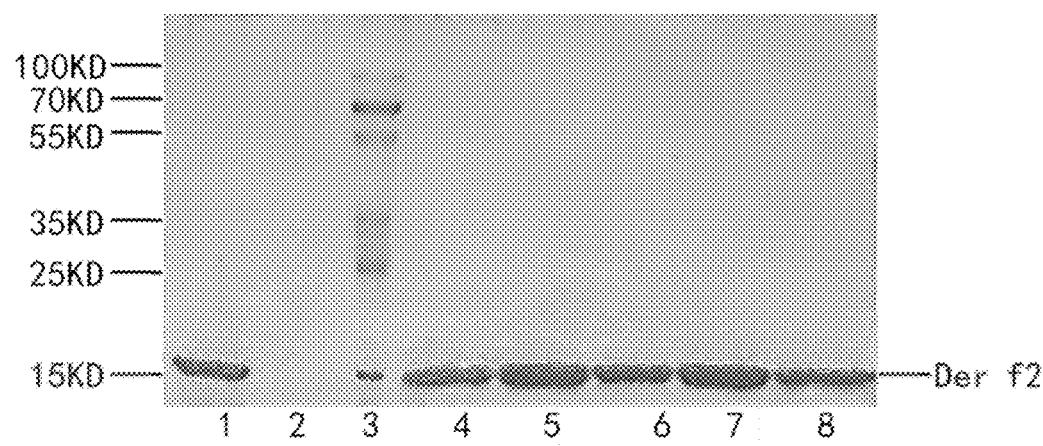

FIG. 10A shows a chromatogram of Der f2 protein by hydrophobic chromatography of the third step and FIG. 10B is a gel electrophoretogram.

FIG. 10A is a chromatogram of Der f2 protein by hydrophobic chromatography of the third step. FIG. 10B is the identification result of hydrophobic chromatography purification of Der f2, wherein lane 1 is Der f2 protein before purification by hydrophobic chromatography, lane 2 is Der f2 penetrate by hydrophobic chromatography, lane 3 represents 11-100 KD non-pre-stained protein markers, and lane 4-10 represent the elution of each tube.

FIG. 11 is the sequencing of N-terminal amino acids of Der f2 proteins.

Figure 12:
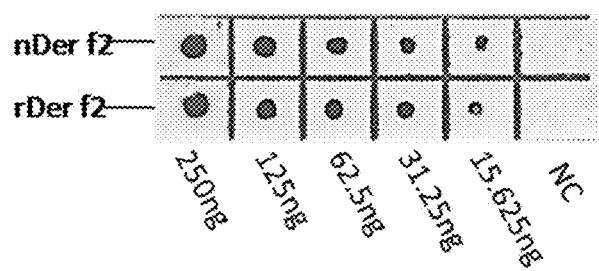

FIG. 12 is a comparison of the reactivity to serum of recombinant Der f2 and natural Der f2 wherein nDer f2 represents the natural Der f2 protein, rDer f2 represents the recombinant Der f2 protein, and NC represents a PBS solution at pH 7.4.

Figure 13:
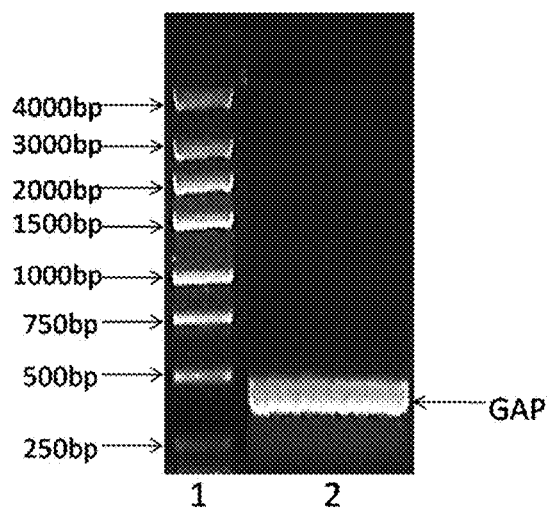

FIG. 13 is an agarose gel electrophoretogram of a PCR-amplified GAP gene, wherein lane 1 represents 250 bp DNA ladder and lane 2 represents the GAP gene.

Figure 14:
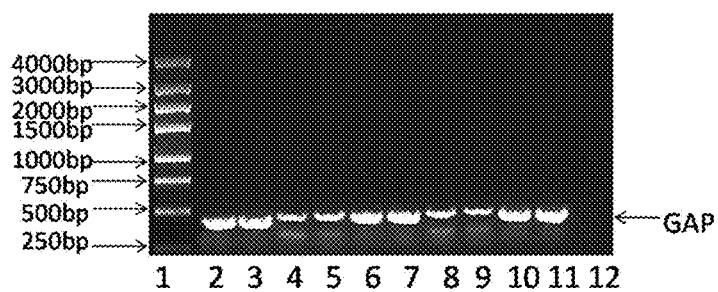

FIG. 14 is an agarose gel electrophoretogram of positive clone of GAP gene T-vector identified by PCR, wherein lane 1 represents 250 bp DNA ladder, lanes 2-11 represent positive clones obtained by blue-white screening, and lane 12 represents a negative clone obtained by blue-white screening.

Figure 15:
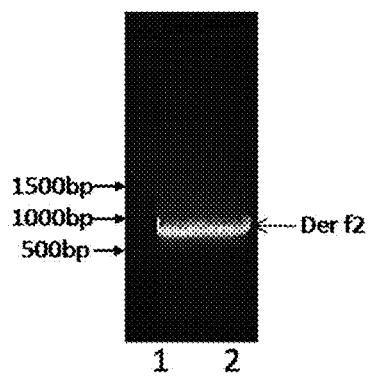

FIG. 15 is an agarose gel electrophoretogram of a PCR-amplified Der f2 gene, wherein lane 1 represents 500 bp DNA ladder and lane 2 represents the Der f2 gene.

Figure 16:
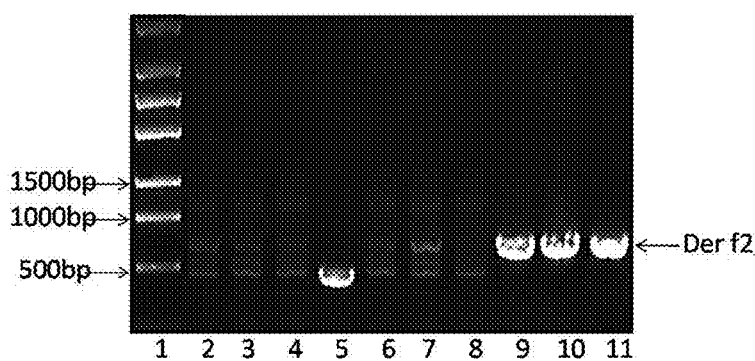

FIG. 16 is an agarose gel electrophoretogram of Der f2 gene T-vector clone identified by PCR, wherein lane 1 represents 500 bp DNA ladder, lanes 2-10 represent positive clones obtained by blue-white screening, in which only lane 9 and 10 are positive clones, other lanes are false positive clones, and lane 17 represents a positive control (Der f2 gene).

Figure 17A:
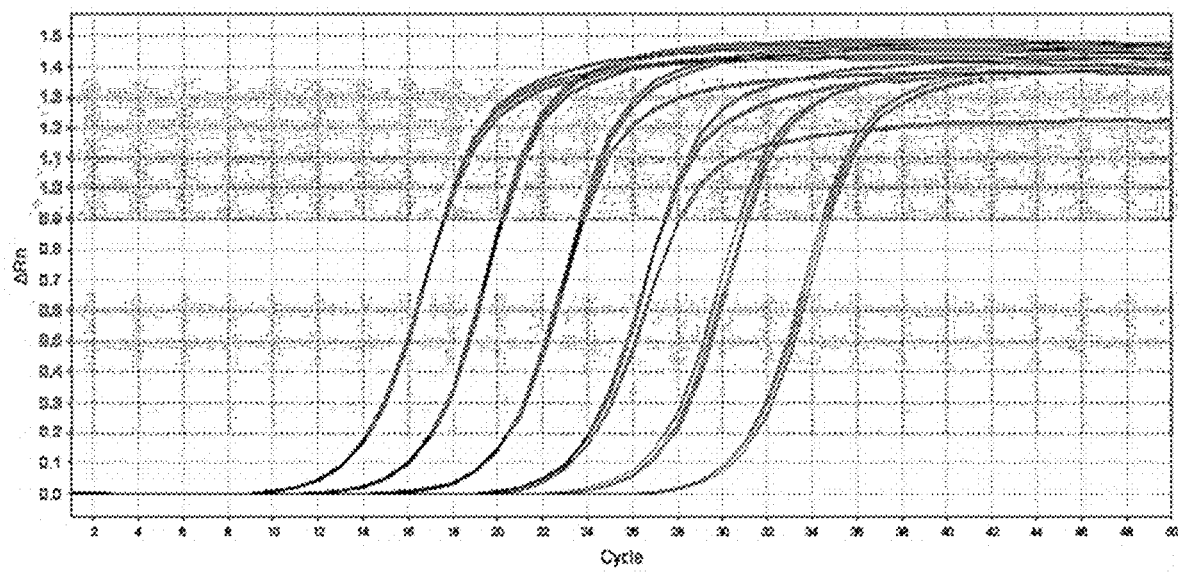
Figure 17B:
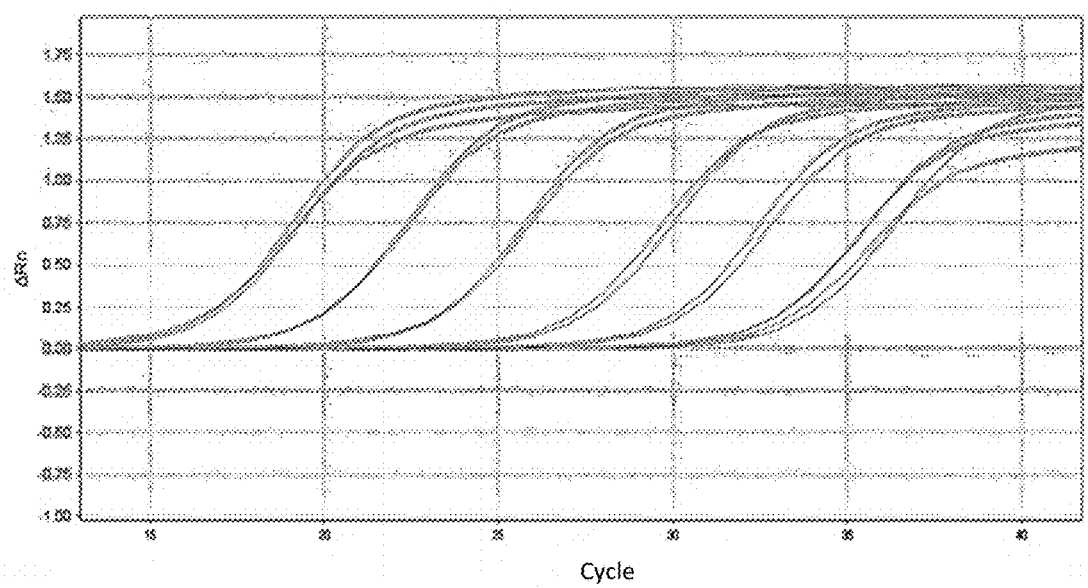

FIGS. 17A and 17B show amplification curves of a standard plasmid.

FIG. 17A shows amplification curves of the standard plasmid T-GAP, and FIG. 17B shows amplification curves of the standard plasmid T-Der f2.

Figure 18A:
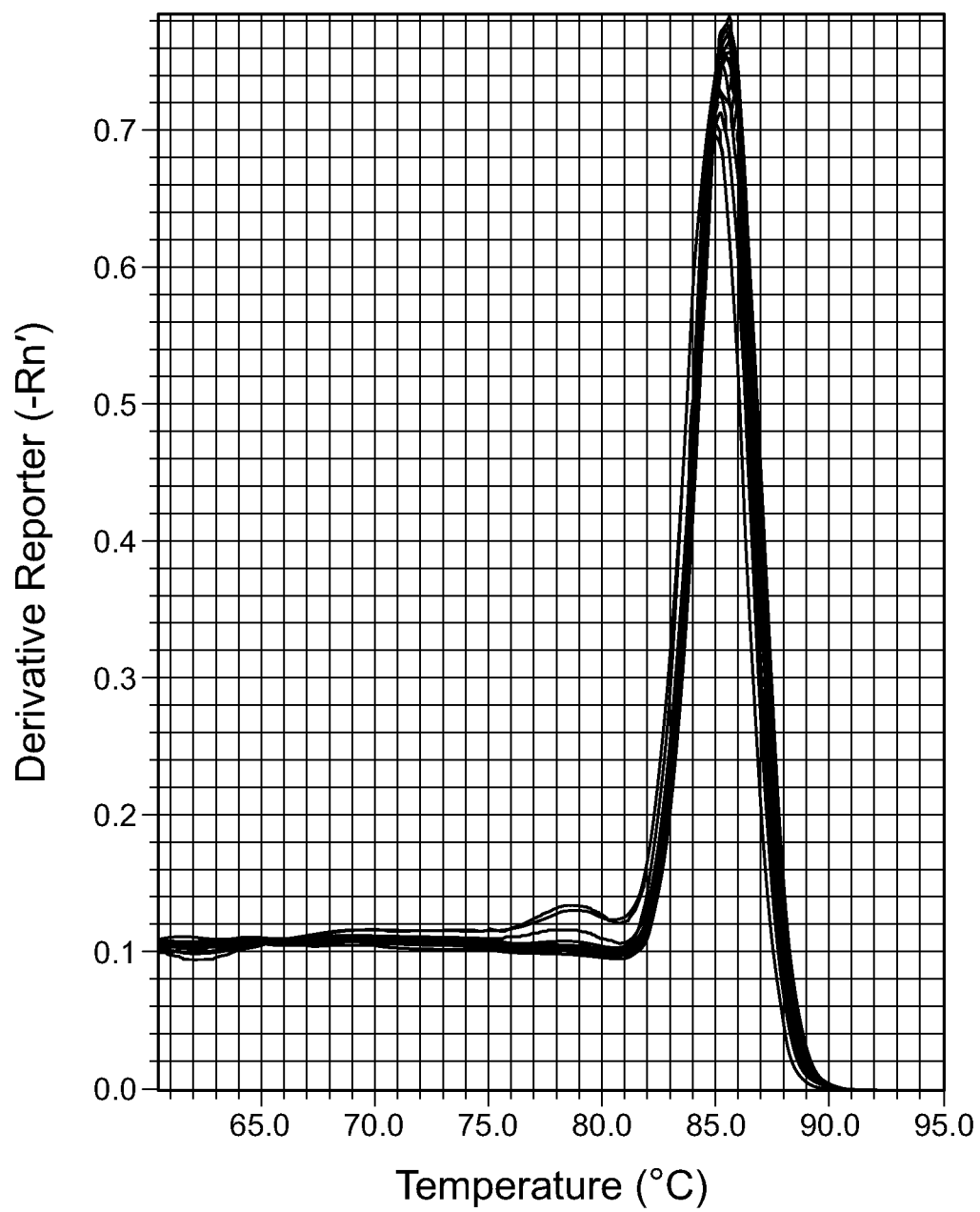
Figure 18B:
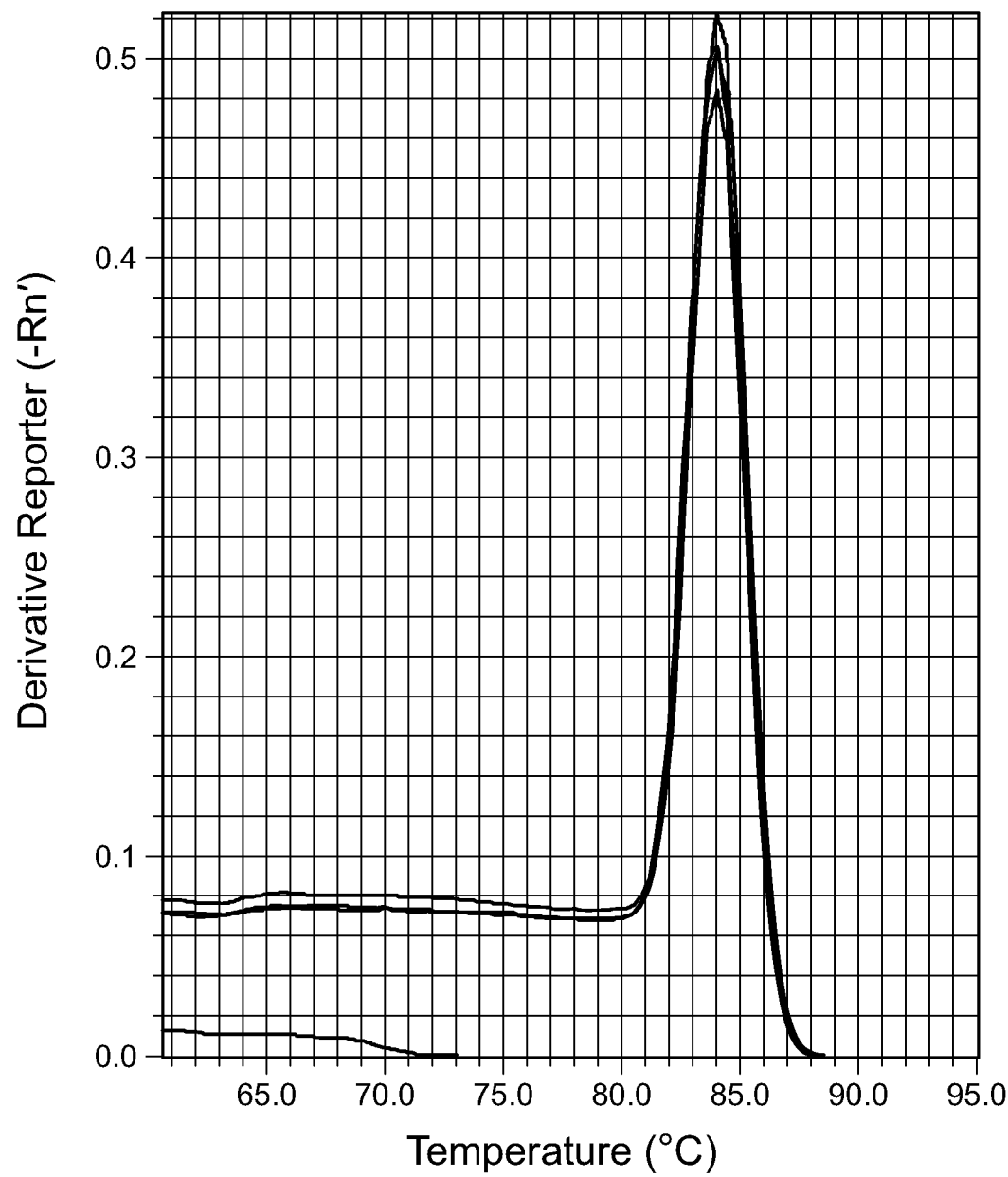

FIGS. 18A and 18B show melting curves of a standard plasmid.

FIG. 18A shows melting curves of the standard plasmid T-GAP, and FIG. 18B shows melting curves of the standard plasmid T-Der f2.

Figure 19A:
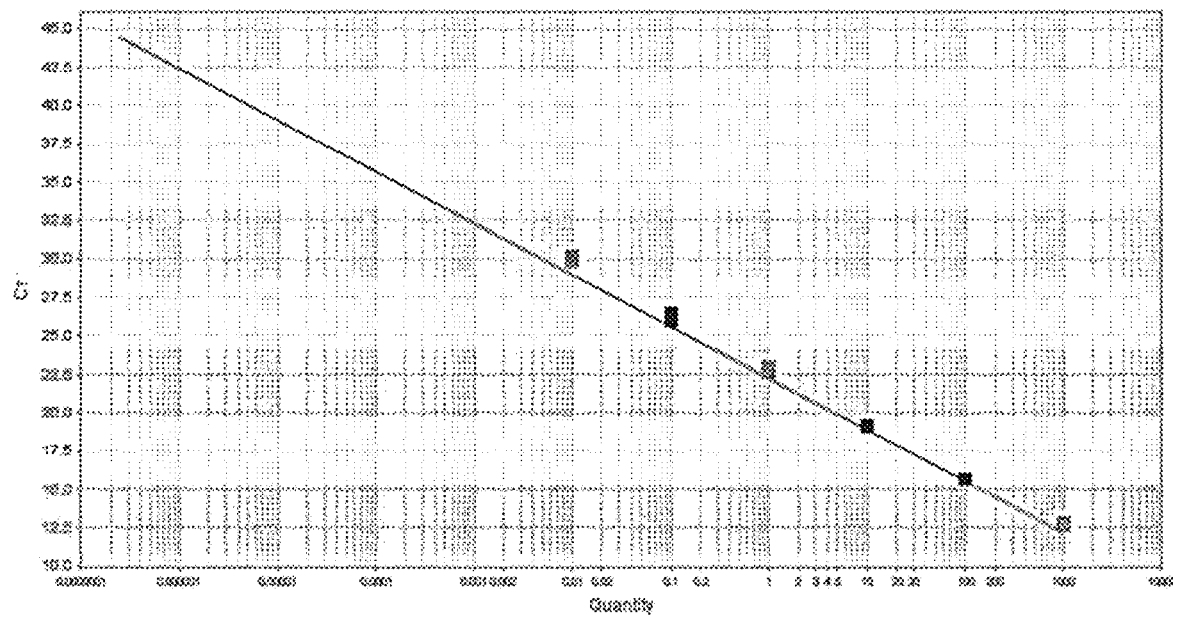
Figure 19B:
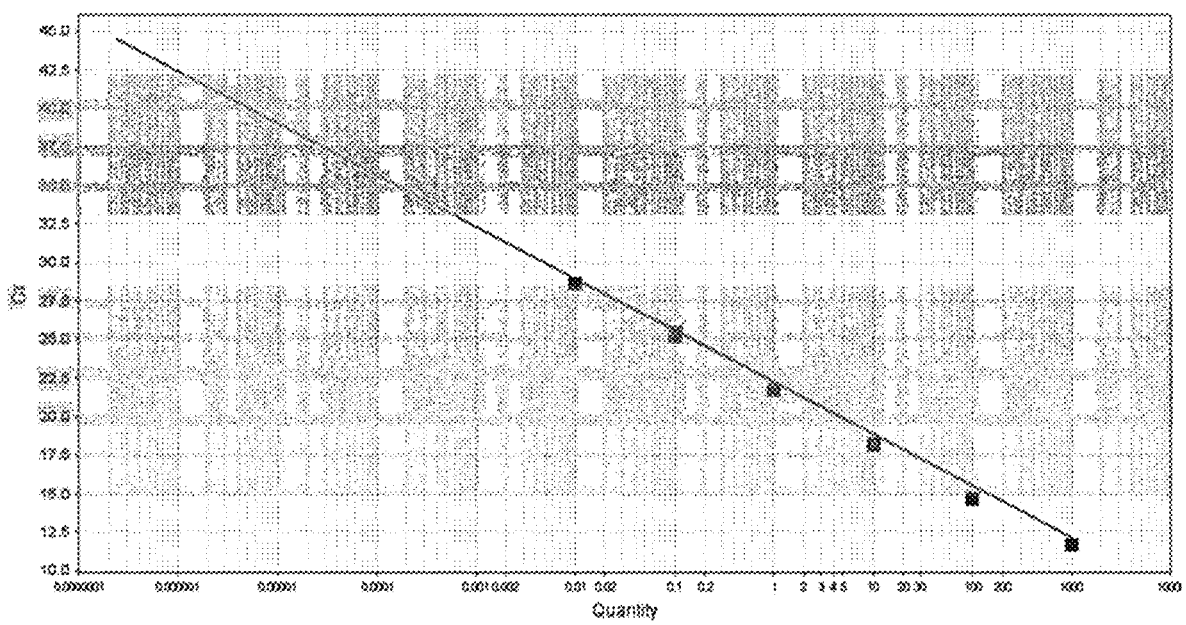

FIGS. 19A and 19B show a standard curve of a standard plasmid.

FIG. 19A shows a standard curve of the standard plasmid T-GAP, and FIG. 19B shows a standard curve of the standard plasmid T-Der f2.

Figure 20A:
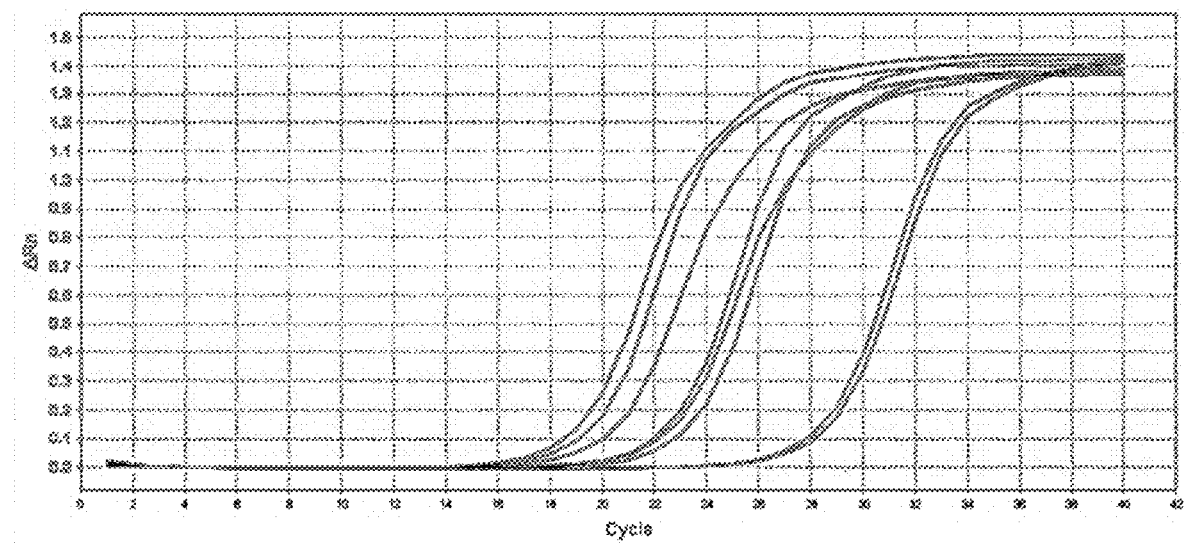
Figure 20B:
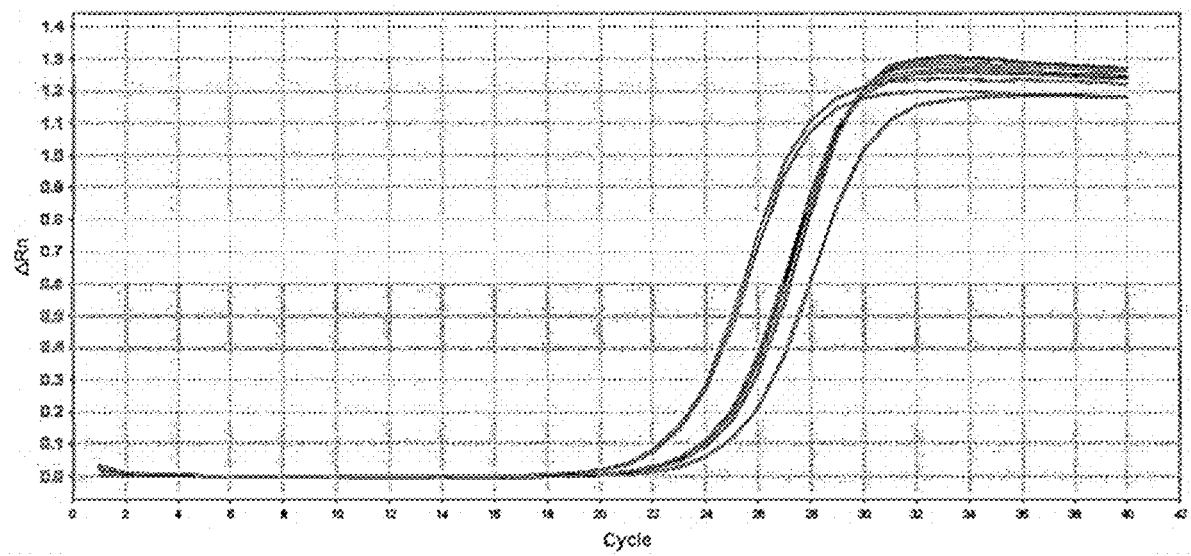

FIGS. 20A and 20B show amplification curves of samples to be tested.

FIG. 20A shows amplification curves obtained when the samples to be tested are amplified with GAP-1 and GAP-2 as primers, and FIG. 20B shows amplification curves obtained when the samples to be tested are amplified with 5' AOX and 3' AOX as primers.

Figure 21A:
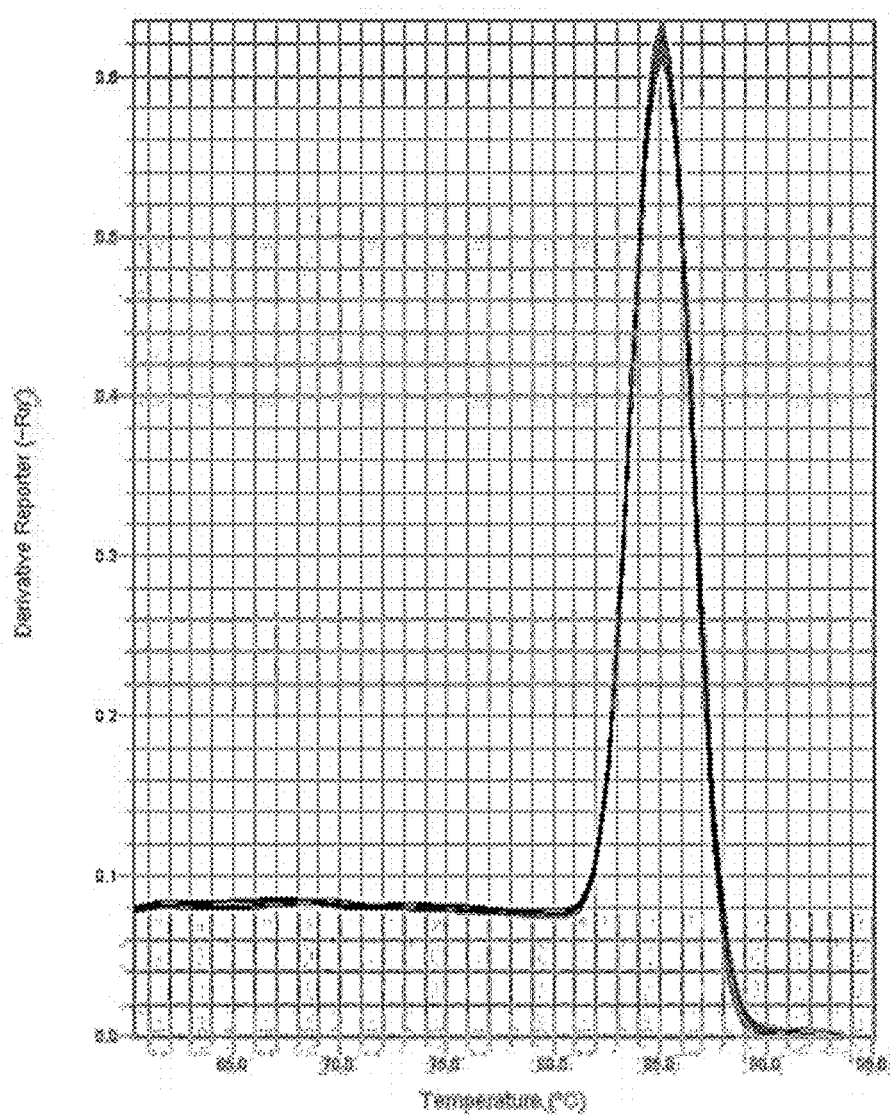
Figure 21B:
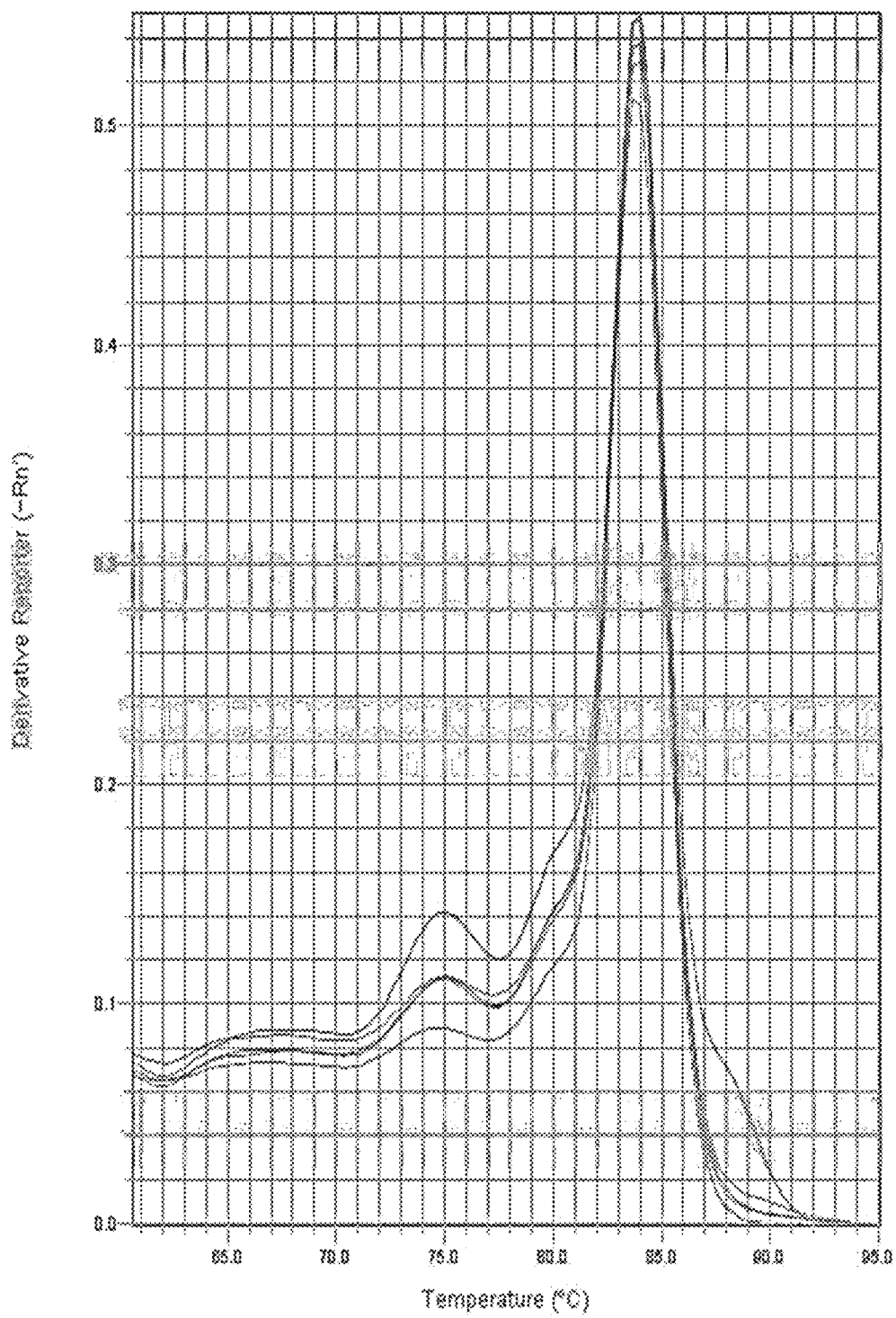

FIGS. 21A and 21B show melting curves of samples to be tested.

FIG. 21A shows melting curves obtained when the samples to be tested are amplified with GAP-1 and GAP-2 as primers, and FIG. 21B shows melting curves obtained when the samples to be tested are amplified with 5' AOX and 3' AOX as primers.

DETAILED DESCRIPTION OF THE INVENTION

The invention is further illustrated below in conjunction with specific examples. It should be understood that the examples referred to are merely illustrative of the invention and are not intended to limit the scope of the present invention.

Example 1 Codon Optimization of Recombinant Der f2

Based on the DNA sequence of Der f2 disclosed in GenBank (GenBank accession no. EF139432.1), as shown in SEQ ID No: 2, the inventors performed codon optimization of the gene to obtain the Der f2 gene of the present invention of which the nucleotide sequence is as shown in SEQ ID No: 1 and the amino acid sequence is as shown in SEQ ID No: 3. Comparison of each parameter before and after codon optimization of the Der f2 is as follows:

1. Codon Adaptation Index (CAI)

As can be seen from FIG. 2A, the codon adaptation index (CAI) of the original Der f2 gene in the *Pichia pastoris* expression system before codon optimization is 0.80. As can be seen from FIG. 2B, the Der f2 gene has a CAI index of 0.90 in the *Pichia pastoris* expression system after codon optimization. Usually, when CAI=1, it is considered that the gene is in the most ideal expression state in the expression system. The lower the CAI index, the worse the expression level of the gene in the host. Thus, it can be seen the gene sequence obtained by codon optimization can increase the expression level of the Der f2 gene in the *Pichia pastoris* expression system.

2. Optimal Codon Usage Frequency (FOP)

As can be seen from FIG. 3A, based on the *Pichia pastoris* expression vector, the occurrence percentage of the low-utilization codon (codon with a utilization rate less than 40%) of the Der f2 gene sequence is 5% before codon optimization. This unoptimized gene uses tandem rare codons that may reduce translation efficiency and even disintegrate a translation assembly. As can be seen from FIG. 3B, the Der f2 gene has a low utilization codon frequency of 0 in the *Pichia pastoris* system after codon optimization.

3. GC Base Content (GC Curve)

The ideal distribution region of GC content is 30%-70%, and any peak outside this region will affect transcription and translation efficiency to varying degrees. As can be seen from the comparison of the average GC base content distribution region plots of the Der f2 gene in FIG. 4A and FIG. 4B, FIG. 4A shows the average GC base content of the Der f2 gene being 39.37%, and FIG. 4B shows that the peaks of GC content appearing outside the 30%-70% region are removed after optimization, and finally the average GC base content of optimized Der f2 is 44.93%.

Example 2: Construction of an Expression Plasmid Containing the Der f2 Gene

A sequence of EcoRI restriction site was introduced at the 5' end, and a sequence of XhoI restriction site was introduced at the 3' end of the codon-optimized Der f2, and then full gene synthesis was performed. The synthesized gene fragment was constructed into the pUC57 plasmid supplied by GenScript (Nanjing) Co., Ltd., thereby obtaining a plasmid for long-term preservation, denoted as pUC57-Der f2 plasmid.

PCR amplification was performed using the pUC57-Der f2 plasmid as a template, and primers of following sequences:

```
upstream primer (SEQ ID No: 4):
M13 F:
TGT AAA ACG ACG GCC AGT downstream primer (SEQ ID No: 5):
M13 R:
CAG GAA ACA GCT ATG AC
```

The total volume of the reaction was 50 µL, in which 2.5 µL of each primer at a concentration of 10 µmon was added, 1 µL of dNTP at a concentration of 10 mmol/L was added, and 0.5 µL DNA polymerase being Q5 (#M0491L, purchased from New England BioLabs) at 2 U/µL was added. The reaction conditions were 98° C. for 5 seconds, 55° C. for 45 seconds, and 72° C. for 30 seconds. After 25 cycles, the product was analyzed by 1.0% agarose gel electrophoresis. The results showed that the product size was consistent with the expected size (results as shown in FIG. 5). The product was digested with EcoRI (#R0101S, purchased from New England BioLabs) and XhoI (#R0189S, purchased from New England BioLabs), respectively, and electrophoresed on 1% agarose gel to obtain a gene product, which was purified using a DNA gel recovery kit (DP214, purchased from Tiangen Biotech (Beijing) Co., Ltd.). The purified product was ligated to pPICZA plasmid (purchased from Invitrogen) with T4 ligase (#M0202S, purchased from New England BioLabs), and transformed into DH5a competent cells (CB101, purchased from Tiangen Biotech (Beijing) Co., Ltd.) and cultured in an LB solid medium containing bleomycin (purchased from Invitrogen) at 37° C. overnight. On the second day, the positive clones were picked and sequenced, and the sequence was found identical to the expected sequence by alignment, thereby obtaining the expression plasmid of codon-optimized Der f2, denoted as pPICZ-Der f2 (the plasmid construction was as shown in FIG. 6).

Example 3: Construction of a Pichia pastoris Host Engineering Strain Containing a Recombinant Der f2 Gene Formulation of YPDS solid medium: the medium was formulated according to the instructions of Easy SelectPichia Expression Kit, Invitrogen, comprising 10 g/L yeast extract, 20 g/L peptone, 20 g/L glucose, 15 g/L agarose, and 182 g/L sorbitol.

Electrocompetent cells were prepared according to the method of instructions of Easy SelectPichia Expression Kit, Invitrogen. The plasmid pPICZ-Der f2 obtained in Example 2 was linearized with Sac I restriction endonuclease (#R0156S, purchased from New England Biolabs), and precipitated with ethanol. The linearized vector was electrotransformed into competent cells of *Pichia pastoris* X33. The cells were plated on YPDS solid media and cultured at 30° C. until the transformants grew.

Example 4: Inducible Expression and Identification of Engineering Strains Containing Codon-Optimized Der f2 Gene Formulation of BMGY medium: the medium was formulated according to the instructions of Easy SelectPichia Expression Kit, Invitrogen, comprising 10 g/L yeast extract, 20 g/L peptone, 3 g/L $K_2HPO_4$, 11.8 g/L $KH_2PO_4$, 13.4 g/L YNB, $4\times10^{-4}$ g/L biotin, and 10 g/L glycerin.

Formulation of BMMY medium: the medium was formulated according to the instructions of Easy SelectPichia Expression Kit, Invitrogen, comprising 10 g/L yeast extract, 20 g/L peptone, 3 g/L $K_2HPO_4$, 11.8 g/L $KH_2PO_4$, 13.4 g/L YNB, $4\times10^{-4}$ g/L biotin, and 5 mL/L methanol.

Methanol-Induced Expression of an Engineering Strain of Codon-Optimized Der f2

The host monoclonal engineering strain obtained in Example 3 was picked into a 5 mL BMGY medium and cultured in a 50 mL sterile centrifuge tube at 30° C. and 220 rpm until $OD_{600}$ reaches 1.0-2.0. 1 mL of the culture was stored, and the remaining strain solution was resuspended and transferred to BMMY for induced expression at a small scale, and methanol was supplemented every 24 hours to a final concentration of 1%. One week later, the supernatant of the strain solution was collected by centrifugation, and analyzed by SDS-PAGE gel electrophoresis and Western blotting. Brightness of expressed product bands was observed. FIGS. 7A and 7B are plots of identification of induced expression of gene engineering strains containing Der f2. As seen from FIGS. 7A and 7B, the Der f2 protein was significantly expressed in the engineering strain.

Example 5: Purification of Recombinant Der f2 Protein

The Der f2 constructed in this invention is obtained mainly by ion exchange and hydrophobic chromatography purification methods. HiTrap SP FF, HiTrap Q FF, and HiTrap Phenyl HP were selected as the chromatographic packings. The specific steps are as follows:

1. Pretreatment of the Fermentation Broth by Impurity Removal

The fermentation broth of host engineering strain containing Der f2 obtained according to Example 4 was centrifuged at a low temperature at 12000 rpm for 15 minutes to collect a supernatant, and the supernatant was ultrafiltrated against a 50 mM sodium acetate buffer at pH 4.0, and filtered through a 0.45 µm filter membrane to obtain a supernatant of the treated fermentation broth.

2. Cation Exchange Chromatography

The treated fermentation broth of the previous step was loaded on a SPFF cation exchange chromatographic column, wherein the equilibration buffer was 50 mM NaAc at pH 4.0, the elution buffer was 50 mM NaAc and 1.0 M NaCl at pH 4.0, isocratic elution was performed at 12%, 25% and 100%, and the sample peaks were mainly concentrated at the 25% elution peak. FIG. 8A is an ion exchange purification chromatogram of Der f2, and FIG. 8B is an SDS-PAGE analysis plot of Der f2 after ion exchange chromatography.

3. Anion Exchange Chromatography

The Der f2 protein peak purified in the previous step was collected, and the sample was ultrafiltrated with a 20 mM $NaH_2PO_4$ solution at pH 6.0, and loaded on a HiTrap Q FF chromatography packing. The equilibration buffer was 20 mM $NaH_2PO_4$ at pH 6.0, and the elution buffer was 20 mM $NaH_2PO_4$ and 1.0 M NaCl at pH 6.0. The flow-through peak of Der f2 was collected.

4. Hydrophobic Chromatography

The flow-through peak of Der f2 from the anion chromatography was collected, and ammonium sulfate was added to a final concentration of 1.5 M. The fermentation broth supernatant treated as above was loaded on a Phenyl HP chromatographic column. The equilibration buffer was 20 mM $NaH_2PO_4$ and 1.5 M $(NH_4)_2SO_4$ at pH 6.0; the elution buffer was 20 mM $NaH_2PO_4$ at pH 6.0, isocratic elution was performed at 25%, 50%, 70%, and 100%, and the Der f2 protein is mainly concentrated at the 75% elution peak. FIG. 10A is hydrophobic chromatography purification chromatogram of Der f2, and FIG. 10B is an SDS-PAGE analysis plot of Der f2 after hydrophobic chromatography. The yield of target protein per liter of fermentation broth is as high as 200 mg or more.

Example 6: Sequence Analysis of N-Terminal Amino Acids of Protein

The determination of N-terminal sequence of proteins and polypeptides is one of the important links in the quality control of pharmaceutical industry. In this experiment, N-terminal sequence analysis based on classical Edman degradation method was used.

The N-terminal sequence of Der f2 protein purified from Example 5 was analyzed by Shimadzu Automatic Protein Peptide Sequencing Instrument (PPSQ-33A, SHIMADZU). The results showed in FIG. 11 that the first five amino acids of N-terminal were DQVDV (SEQ ID No: 11), which indicated that the N-terminal five amino acid sequences of the recombinant Der f2 protein constructed and expressed were identical to those of the natural protein.

Example 7: Analysis of Der f2 Protein Activity

The purified Der f2 protein was dialyzed against a PBS buffer at pH 7.4, and the protein concentration was determined by a BCA protein concentration assay kit (Cat No: 23225, purchased from Pierce), and fold-diluted to 250 ng, 125 ng, 62.5 ng, 31.25 ng, and 15.625 ng. the obtained solution was detected for the reactivity with sera of patients allergic to *Dermatophagoides farinae* by comparing with natural Der f2. FIG. 12 shows that the recombinant Der f2 has substantially identical reactivity with the sera as compared with the natural Der f2, showing that the recombinant Der f2 has a similar biological activity as the natural Der f2.

Example 8: Determination of Gene Copy Number of Recombinant Der f2 Engineering Strain 1. Inoculation X33 strain: the strains were cultured in YPD media for 24 h, the X33 genome was extracted by a genomic extraction kit (purchased from Tiangen Biotech (Beijing) Co., Ltd.), and GAP gene was amplified using the X33 genome as a template, and GAP-1 and GAP-2 as primers of which the sequences are as follows:

```
upstream primer
                                      (SEQ ID No: 6)
GAP-1:
GGTATTAACGGTTTCGGACGTATTG downstream primer
                                      (SEQ ID No: 7)
GAP-2:
GATGTTGACAGGGTCTCTCTCTTGG
```

The total volume of the reaction was 50 μL, in which 2.5 μL of each primer at a concentration of 10 μmon was added, 1 μL of dNTP at a concentration of 10 mmol/L was added, and 0.5 μL DNA polymerase being Taq DNA Polymerase (M0267S, purchased from New England BioLabs) at 2 U/μL was added. The reaction conditions were 94° C. for 10 minutes, 94° C. for 30 seconds, 55° C. for 30 seconds, 68° C. for 30 seconds, and 68° C. for 5 minutes. After 30 cycles, the product was analyzed by 1.0% agarose gel electrophoresis. The results showed that the product size was consistent with the expected size (400 bp) (results as shown in FIG. 13). The obtained gene product was purified by DNA gel recovery kit (DP214, purchased from Tiangen Biotech (Beijing) Co., Ltd.) and ligated into pGM-T vector kit (VT202-01, purchased from Tiangen Biotech (Beijing) Co., Ltd.). The vector was transformed into the Top10 competent cells (CB104, purchased from Tiangen Biotech (Beijing) Co., Ltd.), and cultured at 37° C. overnight on blue-white screening media. On the next day, white clones were picked and identified by PCR for which the primers used were GAP-1 and GAP-2. The PCR reaction conditions were consistent with the above-mentioned conditions. The obtained product was analyzed by 1.0% agarose gel electrophoresis, and the results showed that the product size is consistent with the expected size (400 bp) (results as shown in FIG. 14). The positive clones were sent to GenScript (Nanjing) Co., Ltd. for sequencing, and the sequence was found completely identical to the expected sequence by alignment, thereby obtaining the T vector clone of GAP gene, denoted as T-GAP. The T-GAP clone having a correct sequence was inoculated in an LB liquid medium at 37° C. overnight, and the plasmid was extracted (using a plasmid mini-extract kit DP103, purchased from Tiangen Biotech (Beijing) Co., Ltd.) to obtain a standard plasmid for real-time quantitative PCR.

2. The Der f2 gene was amplified using the pPICZ-Der f2 plasmid of Example 2 as a template, and 5' AOX and 3' AOX as primers with the following sequences:

```
upstream primer (SEQ ID No: 8):
5' AOX:
GACTGGTTCCAATTGACAAGC downstream primer (SEQ ID No: 9):
3' AOX:
GGCAAATGGCATTCTGACAT
```

The total volume of the reaction was 50 μL, in which 2.5 μL of each primer at a concentration of 10 μmon was added, 1 μL of dNTP at a concentration of 10 mmol/L was added, and 0.5 μL DNA polymerase being Taq DNA Polymerase (#M0267S, purchased from New England BioLabs) at 2 U/μL was added. The reaction conditions were 94° C. for 10 minutes, 94° C. for 30 seconds, 49° C. for 30 seconds, and 68° C. for 60 seconds, and 68° C. for 5 minutes. After 30 cycles, the product was analyzed by 1.0% agarose gel electrophoresis. The results showed that the product size was consistent with the expected size (750 bp) (results as shown in FIG. 15). The obtained gene product was purified by DNA gel recovery kit (DP214, purchased from Tiangen Biotech (Beijing) Co., Ltd.) and ligated into pGM-T vector kit (VT202-01, purchased from Tiangen Biotech (Beijing) Co., Ltd.). The vector was transformed into the Top10 competent cells (CB104, purchased from Tiangen Biotech (Beijing) Co., Ltd.), and cultured at 37° C. overnight on blue-white screening media. On the next day, white clones were picked and identified by PCR for which the primers used were 5' AOX and 3' AOX. The PCR reaction conditions were consistent with the above-mentioned conditions. The obtained product was analyzed by 1.0% agarose gel electrophoresis, and the results showed that the product size is consistent with the expected size (750 bp) (results as shown in FIG. 16). The positive clones were sent to GenScript (Nanjing) Co., Ltd. for sequencing, and the sequence was found completely identical to the expected sequence by alignment, thereby obtaining the T vector clone of Der f2, denoted as T-Der f2. The T-Der f2 clone having a correct sequence was inoculated in an LB liquid medium at 37° C. overnight, and the plasmid was extracted using a plasmid mini-extract kit (DP103, purchased from Tiangen Biotech (Beijing) Co., Ltd.) to obtain a standard plasmid for real-time quantitative PCR.

3. Calculation of Gene Copy Number:

The concentration (ng/μL) of the standard plasmid was determined by a nucleic acid microanalyzer (Nanodrop2000, ThermoFisher). Copy numbers of GAP and Der f2 were calculated according to the following formula:

$$\text{Copies}/u = (60.02 \times 10^{23}) \times (\text{ng}/\mu\text{l} \times 10^{-9})/(\text{DNA length} \times 660)$$

4. Processing Samples to be Tested

The pPICZ-Der f2-X33 engineering strain was inoculated in YPD liquid media at 30° C. overnight; and the genome was extracted the next day, and its concentration (ng/μL) and purity were determined by a nucleic acid quantitative microanalyzer.

5. Establishment of a Standard Curve

The standard plasmids of T-GAP and T-Der f2 with known copy numbers were gradiently diluted to $10^8$, $10^7$, $10^6$, $10^5$, $10^4$, and $10^3$ copies/μl, respectively. The fluorescent quantitative PCR were performed using GAP-1 and GAP-2, 5' AOX and 3' AOX as primers, respectively. FIG. 17A shows amplification curves of the standard plasmid T-GAP, FIG. 17B shows amplification curves of the standard plasmid T-Der f2, FIG. 18A shows melting curves of the standard plasmid T-GAP, and FIG. 18B shows melting curves of the standard plasmid T-Der f2. Each gradient was assayed 3 times to verify the repeatability of the standard curve. Standard curves were established with the Ct values as the ordinate and the starting template copy numbers as the abscissa. FIG. 19A shows a standard curve of the standard plasmid T-GAP, and FIG. 19B shows a standard curve of the standard plasmid T-Der f2.

6. Determination of Copy Number of Der f2 Gene in Recombinant Strains

The genome sample of extracted pPICZ-Der f2-X33 was serially 10-fold-diluted to obtain four gradients of stock solution, $10^{-1}$, $10^{-2}$, and $10^{-3}$. Fluorescent quantitative PCR was performed using GAP-1 and GAP-2, 5' AOX and 3' AOX as primers, and each gradient was assayed three times. FIG. 20A shows amplification curves of the samples to be tested with GAP-1 and GAP-2 as primers, FIG. 20B shows amplification curves of the samples to be tested with 5' AOX and 3' AOX as primers, FIG. 21A shows melting curves of the samples to be tested with GAP-1 and GAP-2 as primers, and FIG. 21B shows melting curves of the samples to be tested with 5' AOX and 3' AOX as primers. The GAP gene exists in *Pichia pastoris* in a single copy. Therefore, the copy number of the GAP gene can be used to characterize the initial copy number of the genome in the template. The ratio of the copy number of the Der f2 gene to the copy number of the GAP gene is the copy number of Der f2 gene in the *Pichia pastoris* genome. Table 1 shows the detection results of copy number of the Der f2 gene in the *Pichia pastoris* gene engineering strain, the detected copy number is between 5.58 and 6.42, and finally the copy number of the Der f2 gene in the recombinant strain was averaged to eliminate the system error and determined to be 6.

TABLE 1

Results of copy number of Der f2 in the genome detected by real-time fluorescent quantitative PCR

| DNA concentration | Average Ct value gene copy number ($10^N$)Copy number of Der f2 gene in *Pichia pastoris* genome | | | | |
|---|---|---|---|---|---|
| | GAP gene | Der f2 gene | GAP gene | Der f2 gene | Copy number of the Der f2 gene/copy number of the GAP gene |
| Stock solution | 19.86 | 22.96 | 6.31 | 5.88 | 6.42 |
| $10^{-1}$ | 22.14 | 24.48 | 5.95 | 5.72 | 5.97 |
| $10^{-2}$ | 23.44 | 24.53 | 5.72 | 5.47 | 5.58 |
| $10^{-3}$ | 29.07 | 24.73 | 3.46 | 5.47 | 5.95 |

Example 9: Analysis of the Acting Elements in the Der f2 Genome

There is no stable additional plasmid in *Pichia pastoris*, the expression vector is homologously recombined with the host chromosome, and the exogenous gene expression framework is fully integrated into the chromosome to realize the expression of the exogenous gene; the typical *Pichia pastoris* expression vector contains a regulatory sequence of alcohol oxidase gene, and contains the main structures comprising AOX promoter, multiple cloning site, transcription termination and polyA formation gene sequence (TT), screening markers and the like. The promoter is a cis-element for gene expression regulation and an important element for the genetically engineered expression vector. The important role of the promoter at the transcriptional level determines the gene expression level.

The Der f2 genome was extracted according to the method of Example 8, and the Der f2 gene was amplified from the genome using 5' AOX and 3' AOX as primers according to the method in Step 2 of Example 8. The obtained samples were sent to GenScript (Nanjing) Co., Ltd. to detect the acting element before and after the Der f2 gene which was inserted into the genome. The results of genome sequencing indicated that the Der f2 gene expression framework was integrated into the chromosome of *Pichia pastoris* by a single cross-insertion, which enabled the Der f2 gene to express the gene using the AOX promoter on the yeast chromosome, and thus the expression level was higher.

Generally, the closer the first ATG of the exogenous coding sequence to the ATG of AOX1, the better the expression effect. In the gene construction, the inventors chose an enzyme cleavage site closest to the ATG of AOX1, and found that the Der f2 gene was away from ATG of AOX1 only by 242 bp. In addition, Kozak sequence GCCACCATGG (SEQ ID No: 10) was added in front of Der f2 gene, which can greatly improve transcription and translation efficiency and increase expression efficiency of Der f2 gene in eukaryotes.

The invention claimed is:

1. A DNA sequence encoding a Der f2 protein, wherein said DNA sequence has a base sequence as shown in SEQ ID NO: 1.

2. A vector comprising the DNA sequence of claim 1.

3. A host cell comprising the vector of claim 2, wherein said host cell is a *Pichia pastoris* strain.

4. A method for expressing a recombinant Der f2 protein, comprising the steps of:
   (a) constructing a vector comprising said DNA sequence encoding a Der f2 protein of claim 1;
   (b) linearizing the vector of step A, transferring it into a *Pichia pastoris* strain, and culturing under a suitable condition; and
   (c) recovering a Der f2 fermentation broth and purifying the recombinant Der f2 protein.

5. A method for purifying a recombinant Der f2 protein, comprising the steps of:
   (a) filtering, through a 0.45 μm filter membrane, an ultrafiltered supernatant, wherein the supernatant is obtained by centrifuging the Der f2 fermentation broth in claim 4 at a low temperature and a high speed before ultrafiltration against a 50 mM sodium acetate buffer at pH 4.0;
   (b) passing the Der f2 fermentation broth pretreated in step (a) through a chromatographic separation column pre-equilibrated with a first equilibration buffer comprising 50 mM sodium acetate at pH 4.0, and eluting with a gradient of a first elution buffer to collect a Der f2 protein elution peak, wherein the elution buffer comprises 50 mM sodium acetate and 1.0 M sodium chloride at pH 4.0;
   (c) loading the Der f2 protein elution peak collected in step (b) and subsequently ultrafiltered with a 20 mM phosphate solution at pH 6.0, on an anion chromatographic column, and collecting a Der f2 flow-through peak, wherein the anion chromatographic column is pre-equilibrated with a second equilibration buffer comprising 20 mM phosphate at pH 6.0; and
   (d) adding ammonium sulfate to the Der f2 flow-through peak collected in step (c) to the final concentration of 1.5 M, pH 6.0 to obtain a Der f2 sample, before loading the Der f2 sample to a hydrophobic chromatographic column pre-equilibrated with a third equilibration buffer comprising 1.5 M ammonium sulfate and 20 mM phosphate at pH 6.0, and eluting with a gradient of a second elution buffer comprising 20 mM phosphate at pH 6.0, thereby purifying the recombinant Der f2 protein.

6. The vector of claim 2, wherein said vector is pAO815, pPIC9, pPIC9K, pPIC3.5, pPIC3.5K, pPICZ A, B, C or pGAPZ A, B, C.

7. The host cell of claim 3, wherein the *Pichia pastoris* strain is SMD1168, GS115, KM71, X33 or KM71H.

8. The host cell of claim 7, wherein there is a 242 bp interval between the DNA sequence encoding the Der f2 protein and ATG of AOX1 on *Pichia pastoris*; and the DNA sequence encoding the Der f2 protein is preceded by Kozak sequence GCCACCATGG (SEQ ID NO: 10).

\* \* \* \* \*

SEQUENCE LISTING

<160> NUMBER OF SEQ ID NOS: 11

<210> SEQ ID NO 1
<211> LENGTH: 444
<212> TYPE: DNA
<213> ORGANISM: Dermatophagoides farinae

<400> SEQUENCE: 1

```
atgatctcta agatcttgtg tttgtctttg ttggttgctg ctgttgttgc tgaccaggtt      60
gacgttaagg actgtgctaa caacgagatc aagaaagtta tggttgacgg ttgtcacggt     120
tccgacccat gtattattca cagaggtaag ccattcactt tggaggcttt gttcgacgct     180
aaccagaaca ctaagactgc taagatcgag attaaggctt ccttggacgg tttggagatt     240
gacgttccag gtatcgacac taacgcttgt cactttatga agtgtccatt ggttaagggt     300
cagcagtacg acatcaagta cacttggaat gttccaaaga tcgctccaaa gtccgagaac     360
gttgttgtta ctgttaagtt gatcggtgac aacggtgttt ggcttgtgc tattgctact      420 cacggtaaga tcagagatta atag                                            444
```

<210> SEQ ID NO 2
<211> LENGTH: 441
<212> TYPE: DNA
<213> ORGANISM: Dermatophagoides farinae

<400> SEQUENCE: 2

```
atgatttcca aaatcttgtg cctttcattg ttggtagcag ccgttgttgc cgatcaagtc      60
gatgttaaag attgtgccaa caatgaaatc aaaaaagtaa tggtcgatgg ttgccatggt     120
tctgatccat gcatcatcca tcgtggtaaa ccattcactt tggaagcctt attcgatgcc     180
aaccaaaaca ctaaaaccgc taaaattgaa atcaaagcca gcctcgatgg tcttgaaatt     240
gatgttcccg gtatcgatac caatgcttgc cattttatga atgtccatt ggttaaaggt      300 caacaatatg atatcaaata cacatggaat gtgccgaaaa ttgcaccaaa atctgaaaac     360
gttgtcgtta cagtcaaact tatcggtgat aatggtgttt ggcttgcgc tattgctacc      420 catggtaaaa tccgtgatta a                                               441
```

<210> SEQ ID NO 3
<211> LENGTH: 146
<212> TYPE: PRT
<213> ORGANISM: Dermatophagoides farinae

<400> SEQUENCE: 3

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
                20                  25                  30

Val Met Val Asp Gly Cys His Gly Ser Asp Pro Cys Ile Ile His Arg
            35                  40                  45

Gly Lys Pro Phe Thr Leu Glu Ala Leu Phe Asp Ala Asn Gln Asn Thr
        50                  55                  60

Lys Thr Ala Lys Ile Glu Ile Lys Ala Ser Leu Asp Gly Leu Glu Ile
65                  70                  75                  80

Asp Val Pro Gly Ile Asp Thr Asn Ala Cys His Phe Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Leu Ile
            115                 120                 125

Gly Asp Asn Gly Val Leu Ala Cys Ala Ile Ala Thr His Gly Lys Ile
        130                 135                 140

Arg Asp
145

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtaaaacga cggccagt                                                   18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caggaaacag ctatgac                                                    17

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtattaacg gtttcggacg tattg                                           25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatgttgaca gggtctctct cttgg                                           25

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gactggttcc aattgacaag c                                               21

<210> SEQ ID NO 9
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 9
ggcaaatggc attctgacat                                                    20

<210> SEQ ID NO 10
<211> LENGTH: 10
<212> TYPE: DNA
<213> ORGANISM: Artificial Sequence
<220> FEATURE:
<223> OTHER INFORMATION: Kozak sequence

<400> SEQUENCE: 10
gccaccatgg                                                               10

<210> SEQ ID NO 11
<211> LENGTH: 5
<212> TYPE: PRT
<213> ORGANISM: Artificial Sequence
<220> FEATURE:
<223> OTHER INFORMATION: First five amino acids of N-terminal sequence
      of Der f2 protein

<400> SEQUENCE: 11

Asp Gln Val Asp Val
1               5
```